US012761729B2

(12) United States Patent
Komaki

(10) Patent No.: US 12,761,729 B2
(45) **Date of Patent: *Oct. 13, 2026**

(54) EYE MOVEMENT DETECTING DEVICE, ELECTRONIC DEVICE AND SYSTEM

(71) Applicant: Kabushiki Kaisha Toshiba, Tokyo (JP)

(72) Inventor: Hiroaki Komaki, Tachikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/222,612

(22) Filed: May 29, 2025

(65) Prior Publication Data

US 2025/0291414 A1 Sep. 18, 2025

Related U.S. Application Data

(60) Continuation of application No. 18/523,275, filed on Nov. 29, 2023, now Pat. No. 12,554,321, which is a (Continued)

(30) Foreign Application Priority Data

Mar. 19, 2018 (JP) ................................ 2018-051471

(51) Int. Cl.
*G06F 3/01* (2006.01)
*A61B 5/297* (2021.01)
(Continued)

(52) U.S. Cl.
CPC .............. *G06F 3/013* (2013.01); *A61B 5/297* (2021.01); *A61B 5/315* (2021.01); *A61B 5/398* (2021.01);
(Continued)

(58) Field of Classification Search
CPC .......... G06F 3/013; G06F 1/163; G06F 3/011; G06F 3/015; A61B 5/1114; A61B 5/297;
(Continued)

(56) References Cited

U.S. PATENT DOCUMENTS 6,191,892 B1 2/2001 Isaka
8,434,868 B2 5/2013 Sato et al.
(Continued)

FOREIGN PATENT DOCUMENTS

JP 7-49744 A 2/1995
JP 9-274144 A 10/1997
(Continued)

OTHER PUBLICATIONS

Japanese Office Action issued Sep. 30, 2025 in Japanese Patent Application No. 2024-217567 (with unedited computer-generated English Translation), 13 pages.
(Continued)

*Primary Examiner* — Shaheda A Abdin

(74) *Attorney, Agent, or Firm* — Oblon, McClelland, Maier & Neustadt, L.L.P.

(57) ABSTRACT

According to one embodiment, an eye movement detecting device comprises first, second, third, fourth and fifth electrodes. A line connecting the first and the third electrodes passes through the right eye and a line connecting the second and the fourth electrodes passes through the left eye on at least one of a front view, a plan view or a side view. A distance between the fifth and the first electrodes is equal to a distance between the fifth and the second electrodes. A distance between the fifth and the third electrodes is equal to a distance between the fifth and the fourth electrodes. The detector respectively detects a horizontal movement of the right eye and a horizontal movement of the left eye.

4 Claims, 20 Drawing Sheets

Related U.S. Application Data continuation of application No. 17/940,058, filed on Sep. 8, 2022, now Pat. No. 11,886,635, which is a continuation of application No. 17/375,097, filed on Jul. 14, 2021, now Pat. No. 11,481,028, which is a continuation of application No. 16/568,333, filed on Sep. 12, 2019, now abandoned, which is a division of application No. 16/004,851, filed on Jun. 11, 2018, now Pat. No. 10,466,781.

(51) Int. Cl.

| | |
|---|---|
| ***A61B 5/315*** | (2021.01) |
| ***A61B 5/398*** | (2021.01) |
| ***H04N 13/344*** | (2018.01) |
| *G02B 27/01* | (2006.01) |
| *G06Q 10/087* | (2023.01) |

(52) U.S. Cl.
CPC .... *H04N 13/344* (2018.05); *A61B 2562/0209* (2013.01); *G02B 2027/0134* (2013.01); *G02B 27/0172* (2013.01); *G02B 2027/0178* (2013.01); *G06Q 10/087* (2013.01)

(58) Field of Classification Search
CPC ......... A61B 5/315; A61B 5/6803; A61B 5/30; A61B 2562/0209; H04N 13/344; G02B 27/0172; G02B 2027/0134; G02B 2027/0178; G06Q 10/087
See application file for complete search history.

(56) References Cited

U.S. PATENT DOCUMENTS

| | | | | |
|---|---|---|---|---|
| 8,449,116 | B2 | 5/2013 | Sato et al. | |
| 2002/0057228 | A1 | 5/2002 | Fateh et al. | |
| 2010/0201606 | A1* | 8/2010 | Chung | G02B 30/36 345/8 |
| 2011/0170067 | A1 | 7/2011 | Sato | |
| 2011/0178784 | A1 | 7/2011 | Sato et al. | |
| 2012/0032874 | A1 | 2/2012 | Mukawa | |
| 2012/0154557 | A1 | 6/2012 | Perez | |
| 2012/0194419 | A1 | 8/2012 | Osterhout | |
| 2012/0320100 | A1* | 12/2012 | Machida | G02B 27/017 345/690 |
| 2013/0021373 | A1 | 1/2013 | Vaught | |
| 2013/0235169 | A1 | 9/2013 | Kato | |
| 2013/0324881 | A1 | 12/2013 | Kanoh et al. | |
| 2015/0062322 | A1 | 3/2015 | Gustafsson | |
| 2015/0099946 | A1 | 4/2015 | Sahin | |
| 2015/0192774 | A1* | 7/2015 | Watanabe | G06Q 10/08 345/8 |
| 2015/0226969 | A1 | 8/2015 | Tsukahara | |
| 2016/0133051 | A1 | 5/2016 | Aonuma | |
| 2016/0155267 | A1 | 6/2016 | Bean et al. | |
| 2016/0284129 | A1 | 9/2016 | Nishizawa | |
| 2016/0320623 | A1 | 11/2016 | Miyao | |
| 2017/0060252 | A1 | 3/2017 | Komaki et al. | |
| 2017/0160549 | A1 | 6/2017 | Badiali et al. | |
| 2017/0281086 | A1 | 10/2017 | Donaldson | |
| 2019/0286226 | A1 | 9/2019 | Komaki | |

FOREIGN PATENT DOCUMENTS

| | | | |
|---|---|---|---|
| JP | H09271043 | | 10/1997 |
| JP | 11-202256 | | 1/1998 |
| JP | 2000-102036 | A | 4/2000 |
| JP | 2000-259336 | | 9/2000 |
| JP | 2010-152443 | A | 7/2010 |
| JP | 4500992 | B2 | 7/2010 |
| JP | 2011-125692 | | 6/2011 |
| JP | 2011-125693 | | 6/2011 |
| JP | 2012-128854 | A | 7/2012 |
| JP | 2013-172432 | A | 9/2013 |
| JP | 2013-215356 | | 10/2013 |
| JP | 2013-240469 | | 12/2013 |
| JP | 2013-244370 | | 12/2013 |
| JP | 5564300 | B2 | 7/2014 |
| JP | 2014-164572 | A | 9/2014 |
| JP | 2015-19679 | A | 2/2015 |
| JP | 5680481 | B2 | 3/2015 |
| JP | 2015-130173 | A | 7/2015 |
| JP | 5869770 | B2 | 2/2016 |
| JP | 5951465 | B2 | 7/2016 |
| JP | 2016-189120 | A | 11/2016 |
| JP | 2016-192746 | A | 11/2016 |
| JP | 2016-224086 | A | 12/2016 |
| JP | 2017-49468 | A | 3/2017 |
| JP | 2017-49775 | | 3/2017 |
| JP | 2017-67876 | A | 4/2017 |
| JP | 2017-157139 | | 9/2017 |
| JP | 2017-182460 | A | 10/2017 |
| JP | 2017-189498 | A | 10/2017 |
| JP | 2017-206067 | A | 11/2017 |
| JP | 6228516 | B2 | 11/2017 |
| JP | 2017-538990 | A | 12/2017 |
| JP | 2018-503416 | A | 2/2018 |
| JP | 2018-41011 | A | 3/2018 |
| JP | 2018-42004 | A | 3/2018 |
| JP | 2019-25070 | A | 2/2019 |
| JP | 2019-66562 | A | 4/2019 |
| JP | 6774975 | B2 | 10/2020 |
| JP | 2021-9719 | A | 1/2021 |
| JP | 7309830 | B2 | 7/2023 |
| JP | 2023-145446 | A | 10/2023 |
| JP | 7807087 | | 12/2024 |
| JP | 2025-28167 | | 2/2025 |
| KR | 10-2014-0068332 | A | 6/2014 |
| WO | WO 2015/107625 | A1 | 7/2015 |
| WO | WO 2016/140989 | A1 | 9/2016 |
| WO | WO 2016/151581 | A1 | 9/2016 |
| WO | WO 2017/022302 | A1 | 2/2017 |
| WO | WO 2017/112084 | A1 | 6/2017 |
| WO | WO 2018/012207 | A1 | 1/2018 |
| WO | WO 2018/022521 | A1 | 2/2018 |
| WO | WO 2018/022523 | A1 | 2/2018 |

OTHER PUBLICATIONS

Nakamura, Y. "Future prospect of VR / AR technology", 2016, http://www.mri.co.jp/opinion/column/uploadfiles/tec_10.pdf, 8 pages (w/English translation).
Wakui, H., et al. "Detection of Aimless State by the Vergence Angle", Transactions of Japanese Society for Medical and Biological Engineering, vol. 49, No. 5, 2012, https://www.jstage.jst.go.jp/article/jsmbe/49/5/49_5_693/_pdf, 25 pages (w/English translation).
Office Action issued Mar. 5, 2024, in corresponding Japanese Patent Application No. 2023-109262 (w/English Translation), 10 pages.
Japanese Notice of Reasons for Refusal issued Jul. 23, 2024, in Japanese Patent Application No. 2023-109262 w/English Machine translation, 10 pgs.
Japanese Decision to Grant a Patent issued Dec. 3, 2024, in Japanese Patent Application No. 2023-109262 (w/unedited computer-generated English translation), 6 pages.
Japanese Decision to Grant a Patent issued on Feb. 17, 2026 in Japanese Patent Application No. 2024-217567 (with unedited computer-generated English translation), 6 pages.
Office Action mailed Jul. 28, 2026, in Japanese Application No. 2025-088912 filed May 28, 2025 (w/English translation—citing document Nos. 19-21 therein).

* cited by examiner

EYE MOVEMENT DETECTING DEVICE, ELECTRONIC DEVICE AND SYSTEM

CROSS-REFERENCE TO RELATED APPLICATIONS

This application is continuation of and claims benefit under 35 U.S.C. § 120 to U.S. application Ser. No. 18/523,275 filed Nov. 29, 2023, which is a continuation of and claims benefit under 35 U.S.C. § 120 to U.S. application Sr. No. 17/940,058 filed Sep. 8, 2022 (now U.S. Pat. No. 11,886,635 issued Jan. 30, 2024), which is a continuation of and claims benefit under 35 U.S.C. § 120 to U.S. application Ser. No. 17/375,097 filed Jul. 14, 2021 (now U.S. Pat. No. 11,481,028 issued Oct. 25, 2022), which is a continuation of and claims benefit under 35 U.S.C. § 120 to U.S. application Ser. No. 16/568,333 filed Sep. 12, 2019, which is a division of and claims benefit under 35 U.S.C. § 120 to U.S. application Ser. No. 16/004,851 filed Jun. 11, 2018 (now U.S. Pat. No. 10,466,781 issued Nov. 5, 2019), and claims the benefit of priority under 35 U.S.C. § 119 from Japanese Patent Application No. 2018-051471 filed Mar. 19, 2018, the entire contents of each of which are incorporated herein by reference.

FIELD

Embodiments described herein relate generally to an eye movement detecting device, an electronic device including the eye movement detecting device and a system including the electronic device.

BACKGROUND

As one technique of detecting an eye movement, there is electrooculography (EOG). In this technique, potentials of right eye and left eye (hereinafter referred as eye potentials) can be detected by attaching electrodes to the skin close to each of the right eye and the left eye. The eye movement can be detected based at least in part on a pattern of variation in the eye potentials.

Conventional eye movement detecting devices cannot detect a movement of the right eye and that of the left eye individually. Thus, it cannot distinguish whether the right eye and the left eye move in the same direction or in opposite directions.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

DETAILED DESCRIPTION

Figure 1:
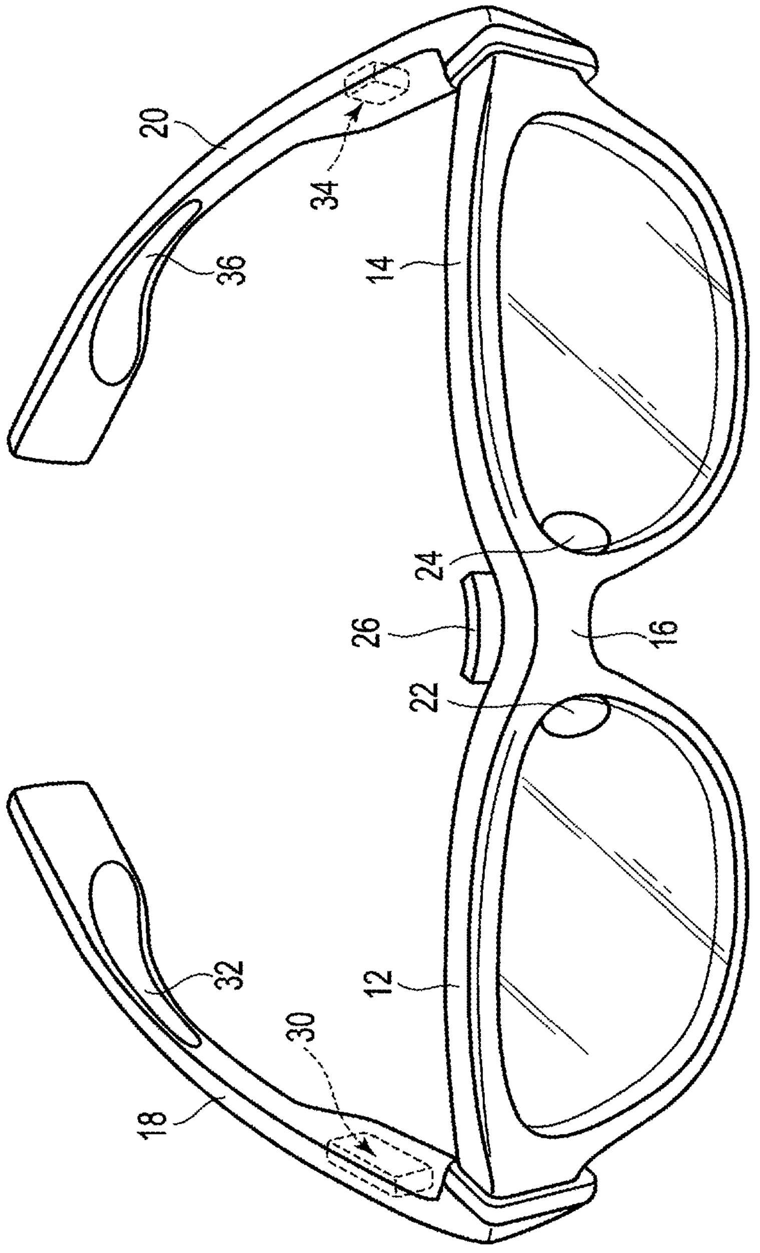
FIG. 1 is a front view of an example of a glass-type wearable device according to a first embodiment.

Various embodiments will be described hereinafter with reference to the accompanying drawings. The disclosure of the embodiments is nothing but one example, and the invention is not limited by the descriptions of the embodiments. Modifications that could easily be conceived by a user with ordinary skill in the art are included in the scope of the disclosure. To clarify the descriptions, the drawings may show, for example, the size and shape of each component more schematically than those in the actual aspect. Elements corresponding to each other in the drawings are denoted by the same reference numeral and their detailed descriptions may be omitted.

In general, according to one embodiment, an eye movement detecting device includes a first electrode on a right of a right eye, a second electrode on a left of a left eye, a third electrode on a left of the right eye, a fourth electrode on a right of the left eye and a fifth electrode, which are contactable with a head. A line connecting the first electrode and the third electrode passes through the right eye. A line connecting the second electrode and the fourth electrode passes through the left eye on at least one of a front view, a plan view or a side view. A distance between the fifth electrode and the first electrode is equal to a distance between the fifth electrode and the second electrode. A distance between the fifth electrode and the third electrode is equal to a distance between the fifth electrode and the fourth electrode. The eye movement detecting device further includes a first detector which detects a first eye potential based at least in part on a difference between the signal from the first electrode and the signal from the second electrode with a signal from the fifth electrode as a reference; a second detector which detects a second eye potential based at least in part on a difference between the signal from the first electrode and the signal from the third electrode with the signal from the fifth electrode as a reference; a third detector which detects a third eye potential based at least in part on a difference between the signal from the second electrode and the signal from the fourth electrode with the signal from the fifth electrode as a reference; and a fourth detector which detects a horizontal movement of the right eye and a horizontal movement of the left eye based at least in part on the first eye potential, the second eye potential and the third eye potential.

The basic information of eyes will be described. The diameter of an adult eye is about 25 mm. The diameter of an eye of a baby immediately after birth is about 17 mm and increases as the baby grows. The interpupillary distance of adult males is about 65 mm. Most commercial stereo cameras are therefore manufactured with a distance between lenses of 65 mm. The interpupillary distance of adult females is several millimeters shorter than that of adult males. The eye potential is several tens of millivolts. The eyes have a positive potential on the cornea side and a negative potential on the retina side. Measuring these potentials on the skin surface, a potential difference (referred to as an eye potential) of several hundreds of microvolts appears.

The rotational movement range of eyes (of general adults) is 50° or less in the left direction and 50° or less in the right direction in the right-and-left movement (also called a horizontal movement), and it is 50° or less in the down direction and 30° or less in the up direction in the up-and-down movement (also called a vertical movement). The angle range in the up direction of the up-and-down movement, in which a user can move his or her eyes at his or her will, is narrow. The reason is as follows. When the eyes are closed, the vertical-direction eye movement range is shifted in the upward direction due to the "Bell's phenomenon" in which the eyes move upward. Note that the convergence angle (the angle at which the line of sight of the right eye and the line of sight of the left eye intersect) is 20° or less.

First Embodiment

Figure 2:
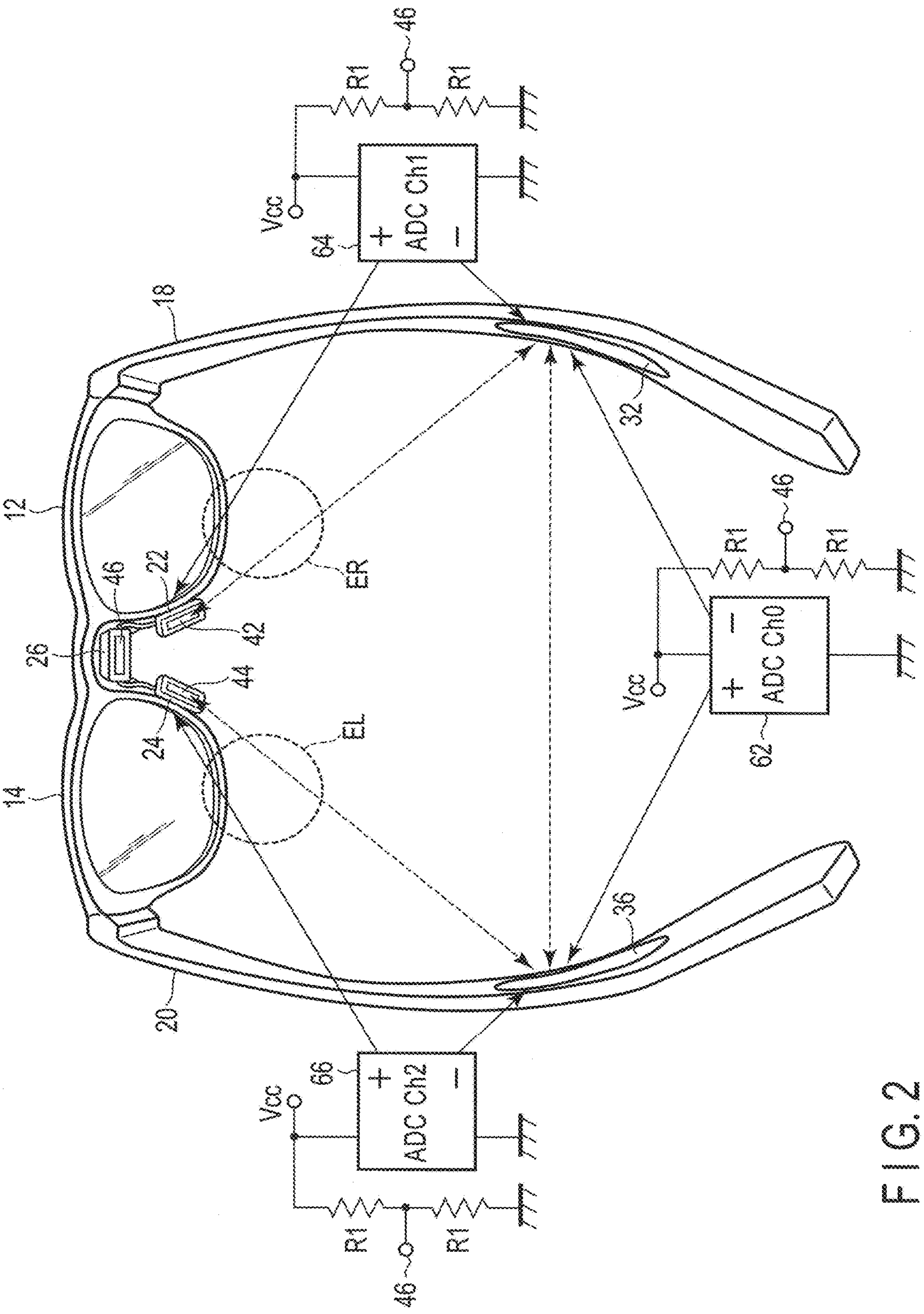
FIG. 2 is a rear top view of the example of the glass-type wearable device.
Figure 3:
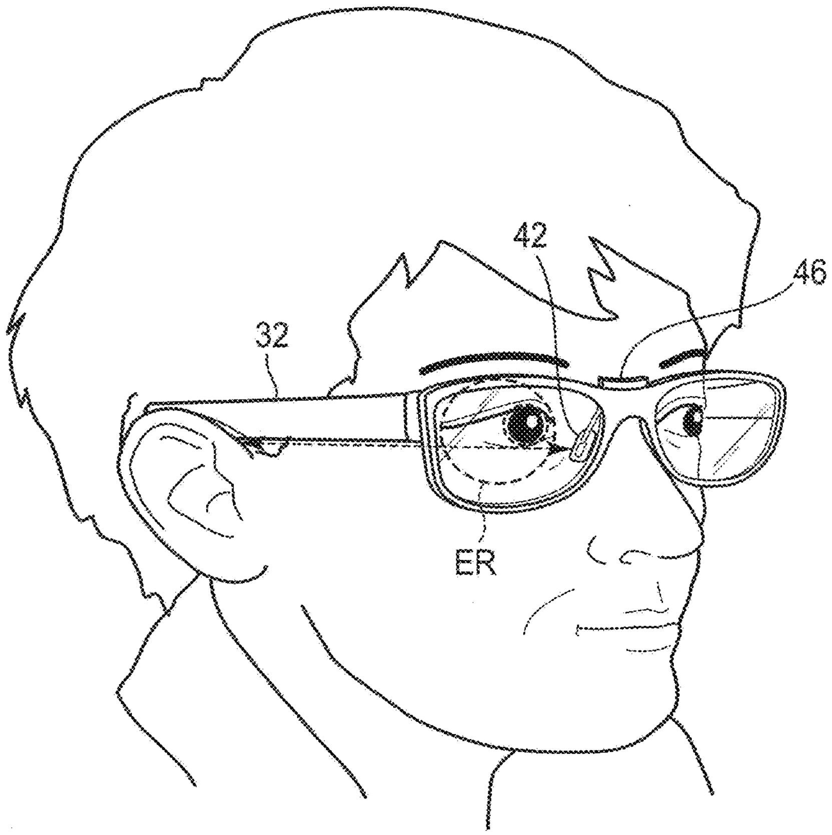
FIG. 3 is a right front view of a user who is wearing the glass-type wearable device.

An example of a configuration of an eye movement detecting device according to an embodiment will be described with reference to FIG. 1, FIG. 2 and FIG. 3. There is a large variety of eye movement detecting devices. This embodiment is directed to an eyewear-type wearable device with the eye movement detecting device. Eyewear includes goggles and glasses (sunglasses are equivalent to glasses) and, in this embodiment, a glass-type wearable device will be described. FIG. 1 is a front view of the example of a glass-type wearable device. FIG. 2 is a rear top view of the example of the glass-type wearable device. FIG. 3 is a right front view of a user who is wearing the glass-type wearable device.

The eye movement includes a vertical movement in which an eye rotates in the up/down direction about a horizontal axis and a horizontal movement in which an eye rotates in the right/left direction about a vertical axis. The vertical movement includes a blink, an eye closing, a wink and the like. The horizontal movement is largely divided into (i) a slow eye movement in which the right eye and the left eye move unconsciously in the same direction, (ii) a line-of-sight movement in which the right eye and the left eye move consciously in the same direction, and (iii) a convergence/divergence movement in which the right eye and the left eye move in opposite directions. The convergence means that the line of sight of the right eye and the line of sight of the left eye intersect and the divergence means that the line of sight of the right eye and the line of sight of the left eye spread. The eye movement is detected based at least in part on variation in the eye potential. The eye potential can be detected by a difference in a voltage between paired electrodes between which an eye is interposed. The eye can be interposed between the paired electrodes in any of the horizontal, vertical, back-and-forth and oblique directions. If the eye potential is detected by the paired electrodes arranged to sandwich an eye vertically, it is possible to detect a blink, an eye closing, a wink and the like. If the eye potential is detected by the paired electrodes arranged to sandwich an eye vertically and horizontally, it is possible to detect a blink, an eye closing, a wink, a slow eye movement and a line-of-sight movement. If the eye potential is detected by the paired electrodes arranged to sandwich an eye in a back-and-forth direction and horizontally, it is possible to detect a slow eye movement, a line-of-sight movement and a convergence/divergence movement.

Placement of Electrodes

The glasses include a right frame 12, a left frame 14 and a bridge 16 connecting the frames 12 and 14 together. In FIG. 1, the glasses are shown from their front and thus the right-side frame in FIG. 1 is the left frame 14. With a detector that detects an eye potential only, lenses or glasses need not be fit into the right frame 12 and the left frame 14. If, however, the user regularly wears his or her glasses, he or she can use glasses with lenses whose power are suitable for the user fit into the right frame 12 and the left frame 14, in place of the user's regular glasses. If the user does not regularly wear the glasses, simple glasses can be fit into the right frame 12 and the left frame 14. Not in the case of the detector that detects an eye potential only, but in the case of a product that detects a line-of-sight movement or a convergence angle variation based at least in part on an eye potential and applies a result of the detection, such as a glass-type wearable device capable of augmented reality (AR) display, a liquid crystal panel or an organic electroluminescence panel for AR display can be fit into at least part of the glasses in the right frame 12 and the left frame 14.

In the first embodiment, in order to detect convergence and divergence, electrodes are placed to sandwich each of the right eye and the left eye from a back-and-forth direction that is in phase with the right eye and the left eye (same vector) on the same plane, and electrodes are placed to sandwich each of the right eye and the left eye from a right-and-left direction that is in phase opposite to the right eye and the left eye (opposite vector) on the same plane.

To detect an eye potential of the right eye ER, as shown in FIG. 2, a right temple electrode 32 is provided on the right of the right eye ER, for example, at a portion of the right temple 18 which is to be put on a user's right ear, and a right nose pad electrode 42 is provided on the left of the right eye ER, for example, on a surface of a right nose pad 22 close to a connecting portion of the right frame 12 and the bridge 16, the surface being in contact with the user's nose. In the plan view (FIG. 2 is regarded as a plan view), the right temple electrode 32 and the right nose pad electrode 42 are placed such that a line connecting these electrodes 32 and 42 passes through the right eye ER.

As shown in the front view (FIG. 1 is regarded as a front view), the right temple electrode 32 is provided on the left of the right eye ER, and the right nose pad electrode 42 (not shown in FIG. 1) is provided on the right of the right eye ER. The right temple electrode 32 and the right nose pad electrode 42 are placed such that a line connecting these electrodes 32 and 42 passes through the right eye ER. In the front view, the right nose pad electrode 42 (not shown in FIG. 1) is provided on the slightly above the right temple electrode 32.

In the side view (not shown), the right temple electrode 32 is provided behind the right eye ER. More specifically, the right temple electrode 32 is provided on the left of the right eye ER in the right-side view and it is provided on the right of the right eye ER in the left-side view. The right nose pad electrode 42 is provided in front of the right eye ER. More specifically, the right nose pad electrode 42 is provided on the right of the right eye ER in the right-side view and it is provided on the left of the right eye ER in the left-side view. The right temple electrode 32 and the right nose pad electrode 42 are placed such that a line connecting these electrodes 32 and 42 passes through the right eye ER.

FIG. 3 shows that the line connecting the right temple electrode 32 and the right nose pad electrode 42 passes through the right eye ER on the front view, plan view and side view of a user's head. Note that the line connecting the two electrodes 32 and 42 is not limited to the passage of the center of the right eye ER but may pass through any portion of the eye. The same is true of the left eye EL though it is hidden by the user's face.

The right temple electrode 32 and the right nose pad electrode 42, which detect an eye potential of the right eye ER, are placed such that the line connecting these electrodes 32 and 42 passes through the right eye ER in the front, plan and side views; however, in at least one of the plan, front and side views, the electrodes 32 and 42 have only to be placed such that the line passes through the right eye ER.

Similarly, in order to detect an eye potential of the left eye EL, as shown in the plan view (FIG. 2), a left nose pad electrode 44 is provided on the right of the left eye EL, for example, on a surface of a left nose pad 24 close to a connecting portion of the left frame 14 and the bridge 16, the surface being in contact with the user's nose, and a left temple electrode 36 is provided on the left of the left eye EL, for example, at a portion of the left temple 20 which is to be put on a user's left ear. The left nose pad electrode 44 and the left temple electrode 36 are placed such that a line connecting these electrodes 44 and 36 passes through the left eye EL.

The right temple electrode 32 and the left temple electrode 36 are symmetric with regard to a straight line orthogonal to the line connecting the right frame 12 and the left frame 14 at the midpoint, the straight line extending to the back of the user's head from the center of the user's nose.

As shown in the front view (FIG. 1), the left nose pad electrode 44 (not shown in FIG. 1) is provided on the left of the left eye EL and the left temple electrode 36 is provided on the right of the left eye EL. The left nose pad electrode 44 and the left temple electrode 36 are placed such that a line connecting these electrodes 44 and 36 passes the left eye EL. In the front view, furthermore, the left nose pad electrode 44 (not shown in FIG. 1) is provided on the slightly above the left temple electrode 36.

In the side view (not shown), the left nose pad electrode 44 is provided in front of the left eye EL. More specifically, the left nose pad electrode 44 is provided on the right of the left eye EL in the right-side view and it is provided on the left of the left eye EL in the left-side view. The left temple electrode 36 is provided behind the left eye EL. More specifically, the left temple electrode 36 is provided on the left of the left eye EL in the right-side view and it is provided on the right of the left eye EL in the left-side view. The left nose pad electrode 44 and the left temple electrode 36 are placed such that a line connecting these electrodes 44 and 36 passes through the left eye EL.

The right temple electrode 32 is provided on the side surface (which is in contact with the right side of the user's head) and the underside surface (which is in contact with the base of the user's right ear) of the right temple 18. When the user wears the glasses, the right temple electrode 32 is brought into contact with a region of the base of the right ear, in which no hard hair grows, by the weight of the temple 18. The left temple electrode 36 is provided on the side surface (which is in contact with the left of the user's head) and the underside surface (which is in contact with the base of the user's left ear) of the left temple 20. When the user wears the glasses, the left temple electrode 36 is brought into contact with a region of the base of the left ear, in which no hard hair grows, by the weight of the temple 20. Accordingly, the right temple electrode 32 and the left temple electrode 36 are brought into close contact with the skin of the user to allow an eye potential to be detected accurately.

Note that the left nose pad electrode 44 and the left temple electrode 36, which detect an eye potential of the left eye EL, have only to be placed such that a line connecting these electrodes 44 and 36 passes through the left eye EL in at least one of the plan, front and side views.

A forehead pad 26 is provided on the inner side of the bridge 16 in contact with the user's forehead. A neutral electrode 46 is provided on the surface of the forehead pad 26, which is in contact with the user's forehead. The neutral electrode 46 is an electrode for securing a neutral potential to detect an eye potential, and is in contact with the skin, such as the forehead. The neutral electrode 46 is provided such that the distance between the neutral electrode 46 and the right temple electrode 32 and the distance between the neutral electrode 46 and the left temple electrode 36 are equal, and the distance between the neutral electrode 46 and the right nose pad electrode 42 and the distance between the neutral electrode 46 and the left nose pad electrode 44 are equal. The neutral electrode 46 is so provided to detect a convergence angle, which will be described later. The convergence angle is detected based at least in part on detection results of eye movements that are symmetrical viewed from the front of the right eye ER and the front of the left eye EL. For example, in an electrocardiogrameutral potential is taken at a portion of the body where the influence of eye movements can be ignored, such as the end of the right leg. Though there is a small influence of eye movements, the eye potential influence, which is exerted upon the neutral electrode by the right eye ER and the left eye EL, can be equalized by taking a neutral potential at a portion influenced equally by the right eye ER and the left eye EL, or the center of the forehead.

The right temple electrode 32, right nose pad electrode 42, left nose pad electrode 44, left temple electrode 36 and neutral electrode 46 may be made of foil such as copper, a metal piece, a metal ball such as stainless steel, a conductive silicon rubber sheet or the like. The electrodes 32, 42, 44 and 36 are also called EOG electrodes because they are intended to detect an eye potential, as will be described later.

EOG Signal

As shown in FIG. 2, a processing unit 30 that detects an eye potential is attached internally or externally to a portion of one of the temples, for example, the right temple 18 close to the right frame 12. A battery 34 for the processing unit 30 is attached internally or externally to a portion of the other temple, for example, the left temple 20, which is close to the frame 12. The processing unit 30 is not designed simply to detect an eye potential but may perform display control in the glass-type wearable device capable of AR display. When the processing unit 30 is provided not inside but outside the glasses, it can be connected to the processing unit 30 by wireless or by wire and, in this case, the battery 34 can be embedded in the processing unit 30. The processing unit 30 can be divided by function into a first processing unit and a second processing unit which are connected to each other by wireless or by wire. Only the first processing unit can be attached to the glasses to detect a signal from the electrode, and the second processing unit can be provided outside the glasses to detect an eye potential from the detected signal from the first processing unit and perform control according to a result of the detection. Mobile terminals such as smartphones may be used as the second processing unit. The second processing unit is not limited to mobile terminals connected directly to the glasses but may include a server connected thereto via a network.

The signal from the right temple electrode 32 is supplied to a negative terminal (−) of a first analog-to-digital converter 62 of channel 0, and the signal from the left temple electrode 36 is supplied to a positive terminal (+) of the first analog-to-digital converter 62. A first EOG signal ADC Cho indicative of a difference between the signal from the right temple electrode 32 and the signal from the left temple electrode 36 is output from the first analog-to-digital converter 62. Since the right temple electrode 32 is placed on the right of the right eye ER and the left eye EL and the left temple electrode 36 is placed on the left of the right eye ER and the left eye EL, the first EOG signal ADC Cho represents the horizontal movement of the right eye ER and the left eye EL.

The signal from the right temple electrode 32 is supplied to a negative terminal (−) of a second analog-to-digital converter 64 of channel 1, and the signal from the right nose pad electrode 42 is supplied to a positive terminal (+) of the second analog-to-digital converter 64. A second EOG signal ADC Ch1 indicative of a difference between the signal from the right temple electrode 32 and the signal from the right nose pad electrode 42 is output from the second analog-to-digital converter 64. Since the right eye ER is sandwiched vertically and horizontally between the right temple electrode 32 and the right nose pad electrode 42, the second EOG signal ADC Ch1 represents the horizontal movement and the vertical movement of the right eye ER.

The signal from the left nose pad electrode 44 is supplied to a positive terminal (+) of a third analog-to-digital converter 66 of channel 2, and the signal from the left temple electrode 36 is supplied to a negative terminal (−) of the second analog-to-digital converter 66. A third EOG signal ADC Ch2 indicative of a difference between the signal from the left nose pad electrode 44 and the signal from the left temple electrode 36 is output from the third analog-to-digital converter 66. Since the left eye EL is sandwiched vertically and horizontally between the left nose pad electrode 44 and the left temple electrode 36, the third EOG signal ADC Ch2 represents the horizontal movement and vertical movement of the left eye EL.

The horizontal positions of the two electrodes 42 and 32 regarding the second EOG signal ADC Ch1 and the horizontal positions of the two electrodes 44 and 36 regarding the third EOG signal ADC Ch2 are opposite (the input terminals of the analog-to-digital converter is reversed). Regarding the second analog-to-digital converter 64, the right temple electrode 32 on the right of the right eye ER is connected to the negative terminal. Regarding the third analog-to-digital converter 66, the left nose pad electrode 44 on the right of the left eye EL is connected to the positive terminal. It is thus possible to detect whether the right eye ER and the left eye EL move horizontally in the same direction or in opposite directions from the waveforms of the second EOG signal ADC Ch1 and third EOG signal ADC Ch2.

Since the voltage signals from the right temple electrode 32, right nose pad electrode 42, left nose pad electrode 44 and left temple electrode 36 are faint, the influence of noise is significant. To cancel the noise, a series circuit of resistors R1 and R2 is connected between the reference analog voltage Vcc (=3.3 V or 5.5 V) of the analog-to-digital converters 62, 64 and 66 and the ground (GND). The neutral electrode 46 is connected to a connecting point of the resistors R1 and R2. The resistors R1 and R2 have the same value of, for example, 1 MΩ. The analog-to-digital converters 62, 64 and 66 can detect analog voltages from 0 V (ground voltage) to the reference analog voltage Vcc and convert an input analog voltage to a digital value in a range of 0 V to 3.3 V (=Vcc) with the midpoint of a detectable range of, for example, ½ voltage of 3.3 V (referred to as a midpoint voltage). The connecting point of the resistors R1 and R2 is connected to a midpoint voltage terminal and the neutral electrode 46 is connected to the connecting point of the resistors R1 and R2. Thus, the midpoint voltage of the analog-to-digital converters 62, 64 and 66 becomes the same as the voltage of the human body (the forehead). Consequently, the midpoint voltage of the analog-to-digital converters 62, 64 and 66 varies with the voltage of the human body, and noise mixed into the voltage signals from the EOG electrodes 32, 42, 44 and 36 is not mixed into digital values of outputs of the analog-to-digital converters 62, 64 and 66. Accordingly, the S/N ratio of eye potential detection can be improved.

Figure 4:
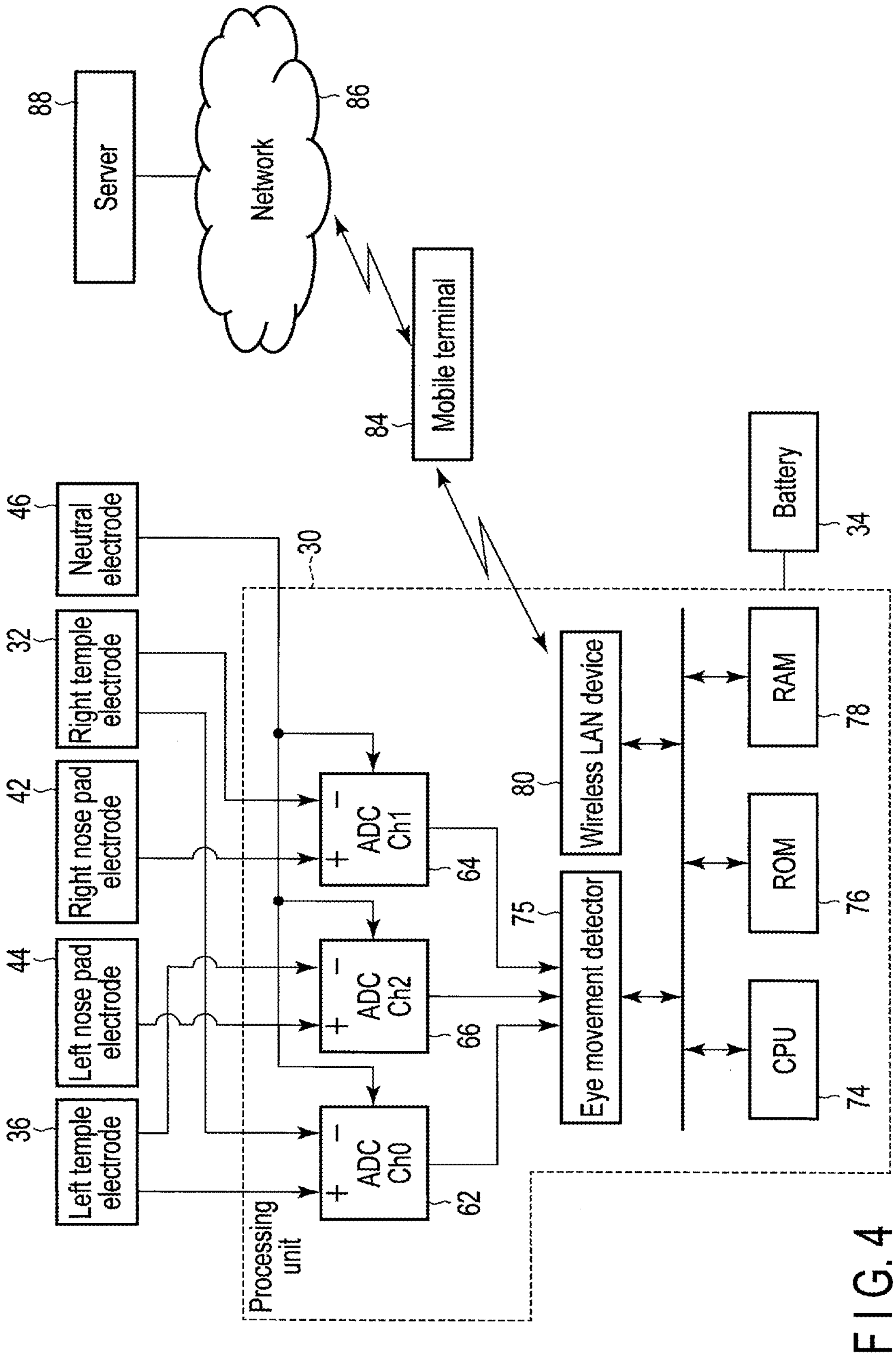
FIG. 4 is a block diagram showing an example of an electrical configuration of the glass-type wearable device.

FIG. 4 is a block diagram showing an example of an electrical configuration of the eye movement detecting device. The processing unit 30 may include the analog-to-digital converters 62, 64 and 66. The analog-to-digital converters 62, 64 and 66 can be attached externally to the processing unit 30.

The signal from the right temple electrode 32 is supplied to the negative terminal (−) of the first analog-to-digital converter 62, and the signal from the left temple electrode 36 is supplied to the positive terminal (+) of the first analog-to-digital converter 62, thus generating an EOG signal ADC Cho of channel 0. The signal from the right temple electrode 32 is supplied to the negative terminal (-) of the second analog-to-digital converter 64, and the signal from the right nose pad electrode 42 is supplied to the positive terminal (+) of the second analog-to-digital converter 64, thus generating an EOG signal ADC Ch1 of channel 1. The signal from the left nose pad electrode 44 is supplied to the positive terminal (+) of the third analog-to-digital converter 66, and the signal from the left temple electrode 36 is supplied to the negative terminal (−) of the second analog-to-digital converter 64, thus generating an EOG signal ADC Ch2 of channel 2.

The signal from the neutral electrode 46 is supplied to the midpoint voltage terminals of the analog-to-digital converters 62, 64 and 66, and the midpoint voltages of the analog-to-digital converters 62, 64 and 66 are considered the voltage of the human body detected by the neutral electrode 46.

The EOG signals output from the analog-to-digital converters 62, 64 and 66 are supplied to an eye movement detector 75 that detects an eye movement (also referred to as eye movement). The eye movement detector 75 can be configured by hardware or software. In the latter case, a CPU 74, a ROM 76 and a RAM 78 are connected to a bus line, and the eye movement detector 75 is also connected to the bus line. The eye movement detector 75 is implemented by the CPU 74 that executes programs stored in the ROM 76. A wireless LAN device 80 is also connected to the bus line, and the processing unit 30 is connected to a mobile terminal 84 such as a smartphone via the wireless LAN device 80. The mobile terminal 84 can be connected to a server 88 via a network 86 such as the Internet. The eye movement detector 75 detects an eye potential based at least in part on the EOG signals output from the analog-to-digital converters 62, 64 and 66. From the detected eye potential, the eye movement detector 75 can detect a horizontal movement (convergence/divergence) of each of the right eye ER and the left eye EL, a horizontal movement (a line-of-sight movement) of the eyes, and a vertical movement (blink, eye closing, etc.). The eye movement detector 75 can also estimate various conditions of the user (for example, the user lacks concentration and is restless, the user is nervous and stressed, the user is tired and cannot concentrate on his or her operations) from the detected eye movement. The eye movement detector 75 estimates other conditions by changing a program to be executed by the CPU 74 what type of eye movement is detected and what type of condition is estimated. A condition to be detected can also be instructed from the mobile terminal 84.

In place of the wireless LAN device 80, a communication device with a communication system such as ZigBee (registered trademark), Bluetooth Low Energy (registered trademark) and Wi-Fi (registered trademark) can be used. The detection results (eye movement detection results, condition estimation results, etc.) of the eye movement detector 75 can be stored temporarily in the RAM 78 and then transmitted to the mobile terminal 84 via a communication device such as the wireless LAN device 80. Alternatively, the detection results can be transmitted to the mobile terminal 84 in real time. The mobile terminal 84 may store the detection results in a built-in memory (not shown) and transfer them to the server 88 via the network 86. In accordance with the detection results, the mobile terminal 84 may start any processing or store the processing results in the built-in memory or transfer the processing results to the server 88 via the network 86. The server 88 may aggregate the detection results of the eye movement detector 75 of a number of wearable devices and the processing results of a number of mobile terminals 84 and analyze what is called big data.

Modifications to Placement of Electrodes

Figure 5:
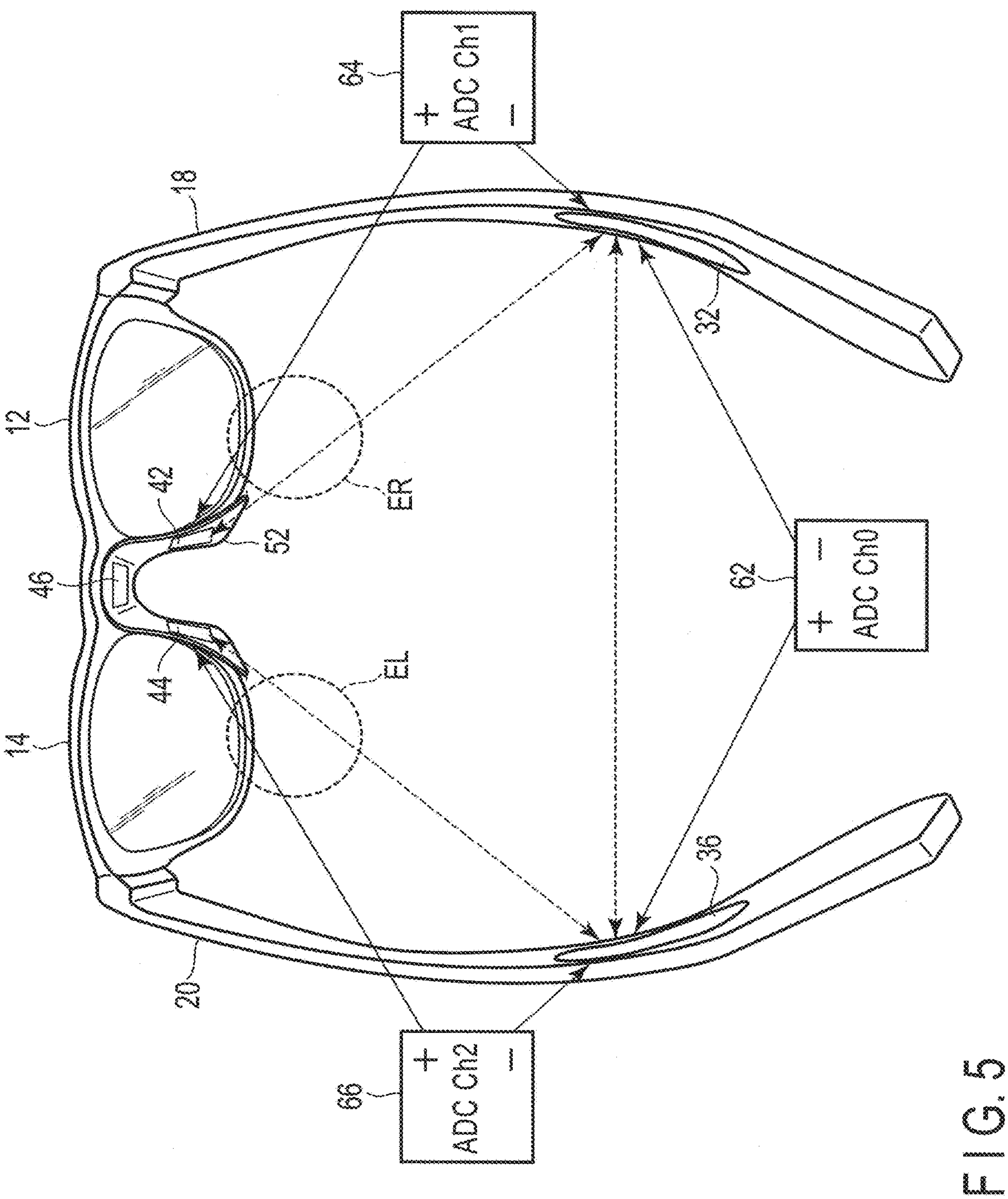
FIG. 5 shows a first modification to the placement of a neutral electrode 46.
Figure 6:
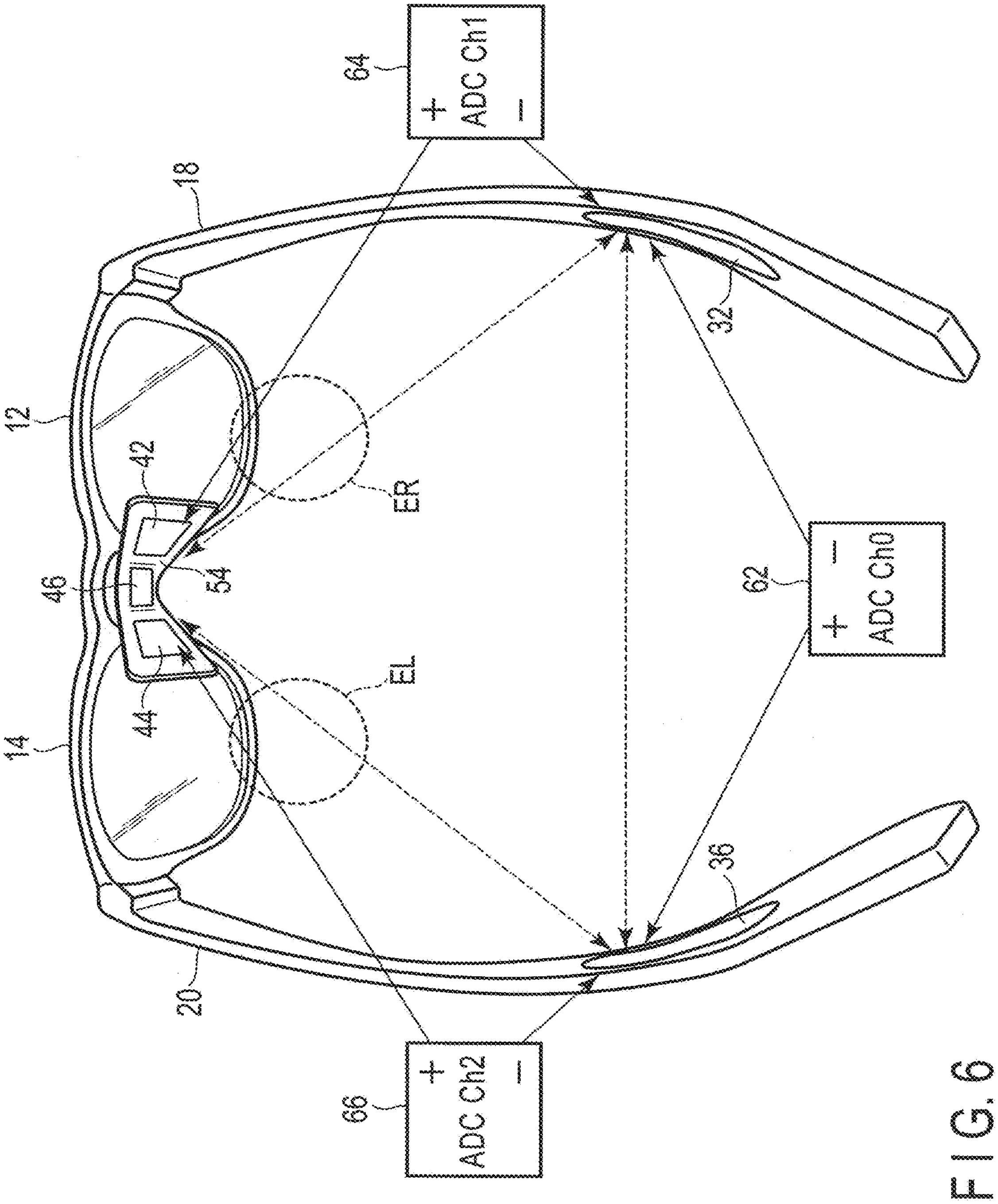
FIG. 6 shows a second modification to the placement of the neutral electrode 46.
Figure 7:
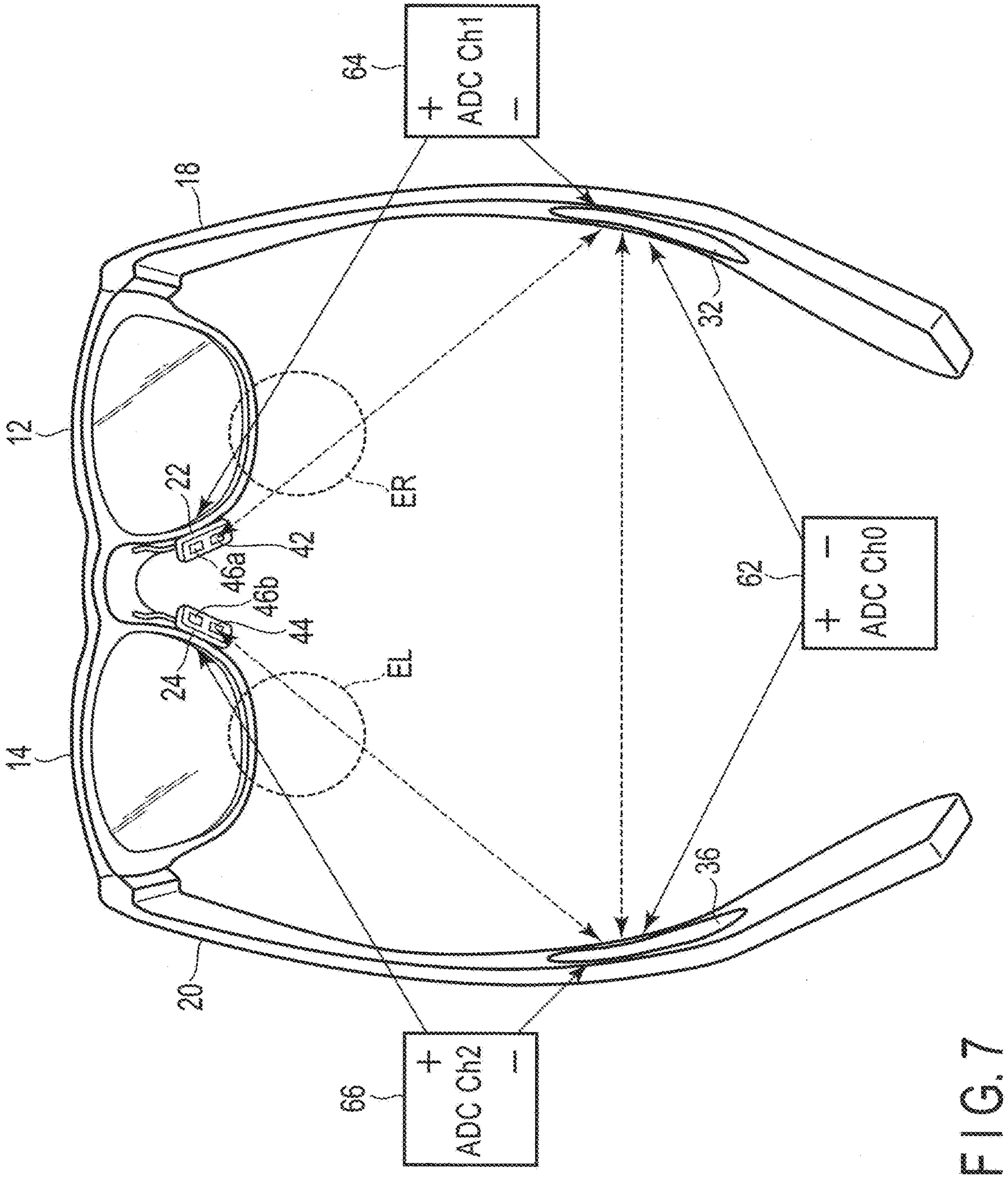
FIG. 7 shows a third modification to the placement of the neutral electrode 46.

FIG. 5, FIG. 6 and FIG. 7 each show a modification to the placement of the neutral electrode 46. In the foregoing description, the right nose pad 22 and the left nose pad 24 are provided separately, but in the modification shown in FIG. 5, an integrated, inverted V-shaped or inverted U-shaped nose pad 52 is provided. The right nose pad electrode 42 is provided on the inner right of the nose pad 52, the left nose pad electrode 44 is provided on the inner left side of the nose pad 52, and the neutral electrode 46 is provided on the inside of a top portion of the inverted V-shaped or inverted U-shaped nose pad 52. The neutral electrode 46 can thus be provided in contact with the user's forehead without using the forehead pad 26.

In the modification shown in FIG. 6, too, an integrated, inverted V-shaped or inverted U-shaped nose pad 54 is provided. The nose pad 54 differs from the nose pad 52 in that the nose pad 54 expands towards the user and the nose pad 52 expands downward. The right nose pad electrode 42 is provided on the right side of the node pad 54, the left nose pad electrode 44 is provided on the left side thereof, and the neutral electrode 46 is provided on the center thereof.

In the modifications shown in FIG. 5 and FIG. 6, a nose pad that is larger than an ordinary one is used. Thus, even though a glass-type wearable device capable of AR display, which is heavier than ordinary glasses, is used for a long time, its weight does not make the user's nose painful.

In the modification shown in FIG. 7, the right nose pad 22 and the left nose pad 24 are used separately, but the forehead pad 26 is unnecessary. In this modification, the right nose pad electrode 42 and a right neutral electrode 46*a* are provided on the surface of the right nose pad 22, which is in contact with the user's nose, and the left nose pad electrode 44 and a left neutral electrode 46*b* are provided on the surface of the left nose pad 24, which is in contact with the user's nose. The right neutral electrode 46*a* and the left neutral electrode 46*b* are electrically short-circuited and become equivalent to one neutral electrode 46.

Relationship between Line-of-Sight Movement and EOG Signal

An example of variation in a waveform of each of the EOG signal ADC Cho output from the analog-to-digital converter 62, EOG signal ADC Ch1 output from the analog-to-digital converter 64 and EOG signal ADC Ch2 output from the analog-to-digital converter 66 will be described with reference to FIG. 8 to FIG. 12. It is assumed that the right eye ER and the left eye EL move horizontally from the state in which the line of sight is in the front direction.

Figure 8:
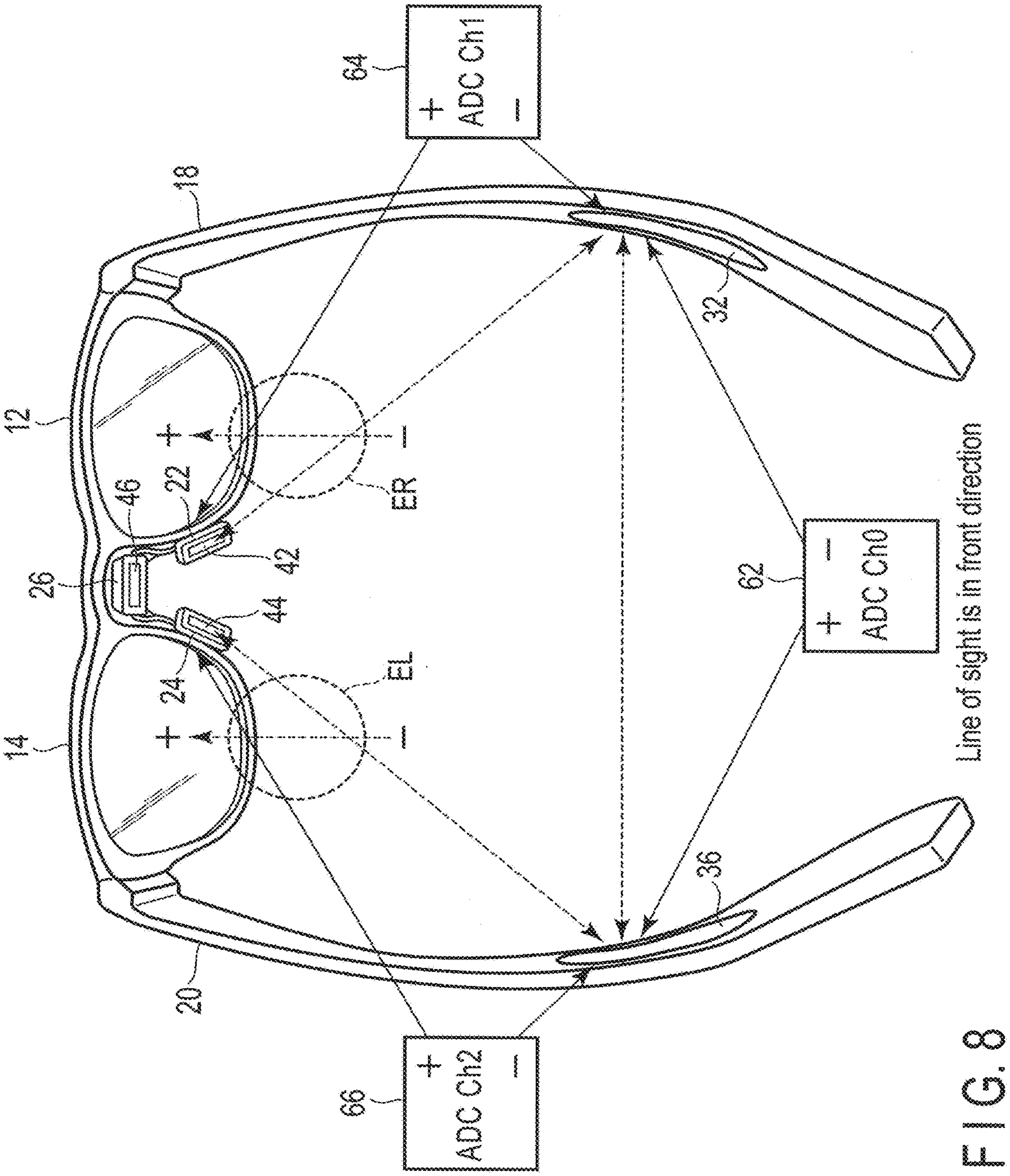
FIG. 8 shows EOG signals in a state where the user's line of sight is in the front direction.
Figure 9:
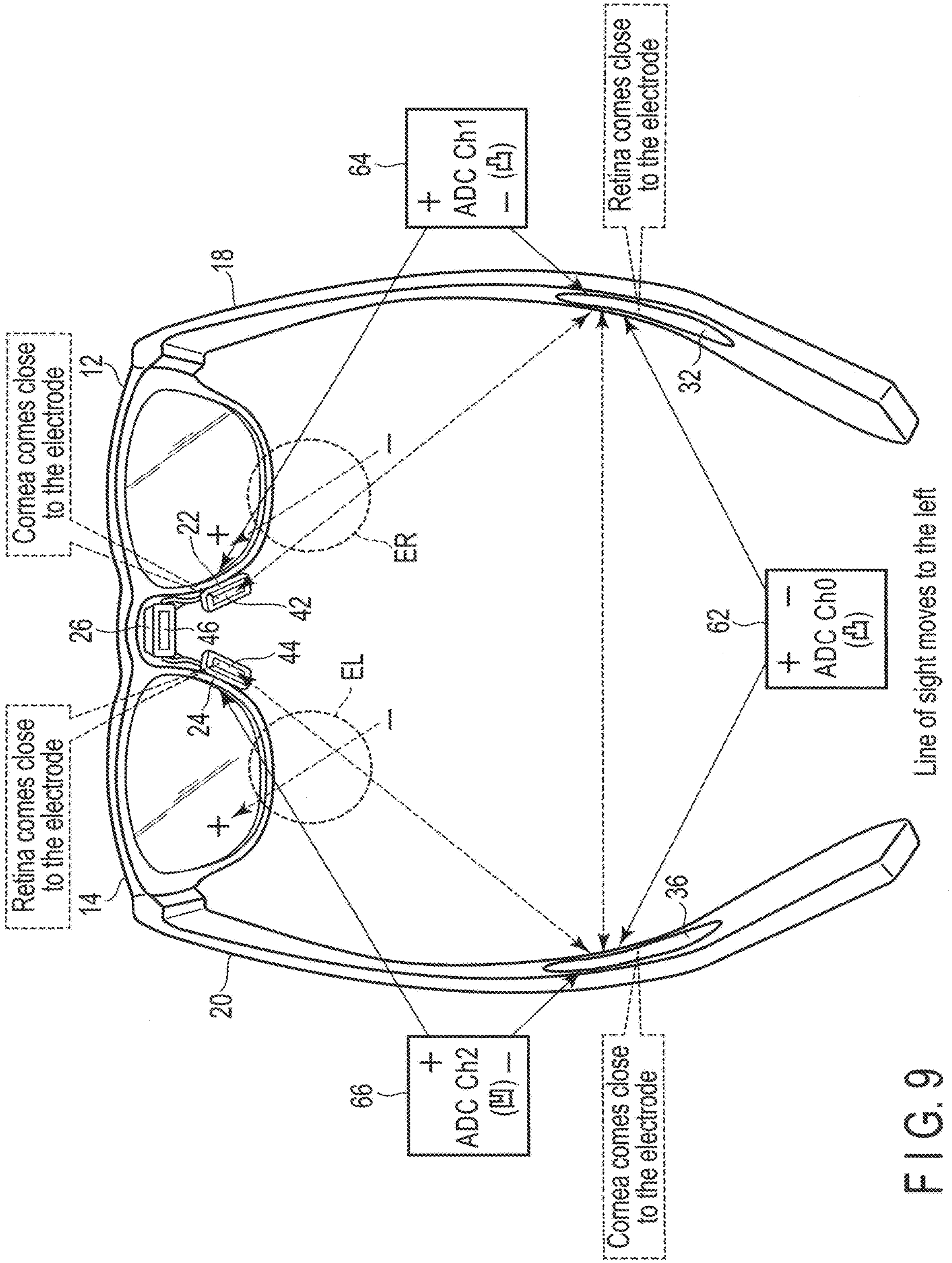
FIG. 9 shows an example of variation in a waveform of the EOG signals when the right eye and the left eye both move to the left from the state where the line of sight is in the front direction.

FIG. 8 shows that the user's line of sight is in the front direction. When the user looks at the infinite far point, the line of sight of the right eye ER and the line of sight of the left eye EL are parallel. When the user looks at the finite far point, the line of sight of the right eye ER and the line of sight of the left eye EL cross at the far point. When the right eye ER and the left eye EL move to the left (the line of sight of the right eye ER and the line of sight of the left eye EL move to the left) from this state, as shown in FIG. 9, the cornea of the right eye ER that is positively charged comes close to the right nose pad electrode 42, and the retina of the right eye ER that is negatively charged comes close to the right temple electrode 32. Similarly, the cornea of the left eye EL that is positively charged comes close to the left temple electrode 36, and the retina of the left eye EL that is negatively charged comes close to the left nose pad electrode 44. When the right eye ER and the left eye EL both move to the right in this state, the state returns to that shown in FIG. 8. Thus, the first EOG signal ADC Ch0 output from the first analog-to-digital converter 62 to which the right temple electrode 32 and the left temple electrode 36 are connected, has a convex waveform (upwardly convex waveform). The second EOG signal ADC Ch1 output from the second analog-to-digital converter 64 to which the right nose pad electrode 42 and the right temple electrode 32 are connected, has a convex waveform (upwardly convex waveform). The third EOG signal ADC Ch2 output from the third analog-to-digital converter 66 to which the left nose pad electrode 44 and the left temple electrode 36 are connected, has a concave waveform (downwardly convex waveform).

Since the right eye ER and the left eye EL move in the same direction (move to the left) as described above, the second EOG signal ADC Ch1 and the third EOG signal ADC Ch2 make waveforms of opposite phases. The first EOG signal ADC Cho makes a waveform of the same phase as that of the waveform of the second EOG signal ADC Ch1 having the same +/−relationship with regard to the right/left relationship as that of the first EOG signal ADC Ch0.

Figure 10:
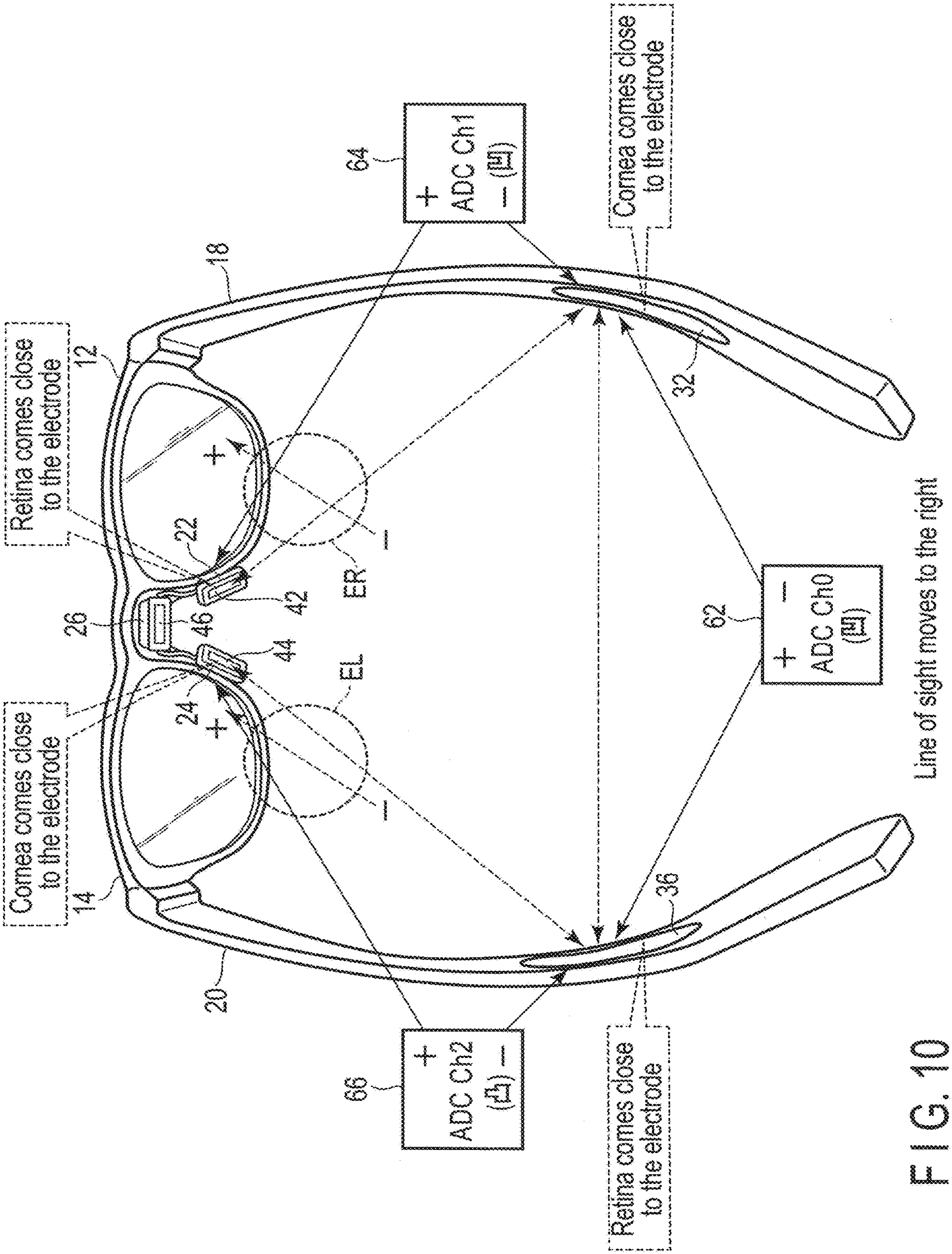
FIG. 10 shows an example of variation in a waveform of the EOG signals when the right eye and the left eye both move to the right from the state where the line of sight is in the front direction.

When the right eye ER and the left eye EL both move to the right (the line of sight of the right eye ER and the line of sight of the left eye EL move to the right), as shown in FIG. 10, from the state in which the line of sight shown in FIG. 8 is in the front direction, the cornea of the right eye ER that is positively charged comes close to the right temple electrode 32, and the retina of the right eye ER that is negatively charged comes close to the right nose pad electrode 42. Similarly, the cornea of the left eye EL that is positively charged comes close to the left nose pad electrode 44, and the retina of the left eye EL that is negatively charged comes close to the left temple electrode 36. When the right eye ER and the left eye EL both move to the left in this state, the state returns to that shown in FIG. 8. Thus, the first EOG signal ADC Ch0 output from the first analog-to-digital converter 62 to which the right temple electrode 32 and the left temple electrode 36 are connected, makes a concave waveform (downwardly convex waveform). The second EOG signal ADC Ch1 output from the second analog-to-digital converter 64 to which the right nose pad electrode 42 and the right temple electrode 32 are connected, makes a concave waveform (downwardly convex waveform). The third EOG signal ADC Ch2 output from the third analog-to-digital converter 66 to which the left nose pad electrode 44 and the left temple electrode 36 are connected, makes a convex waveform (upwardly convex waveform).

Since the right eye ER and the left eye EL move in the same direction (move to the right) as described above, the second EOG signal ADC Ch1 and the third EOG signal ADC Ch2 make waveforms of opposite phases. However, the phase of the waveforms is opposite to that in the case where the right eye ER and the left eye EL both move to the left. The first EOG signal ADC Cho makes a waveform of the same phase as that of the waveform of the second EOG signal ADC Ch1 having the same +/−relationship with regard to the right/left relationship as that of the first EOG signal ADC Ch0. However, the phase of the waveform of the first EOG signal ADC Ch0 in the case where the right eye ER and the left eye EL both move to the right is opposite to that of the waveform of the first EOG signal ADC Ch0 in the case where the right eye ER and the left eye EL both move to the left.

Figure 11:
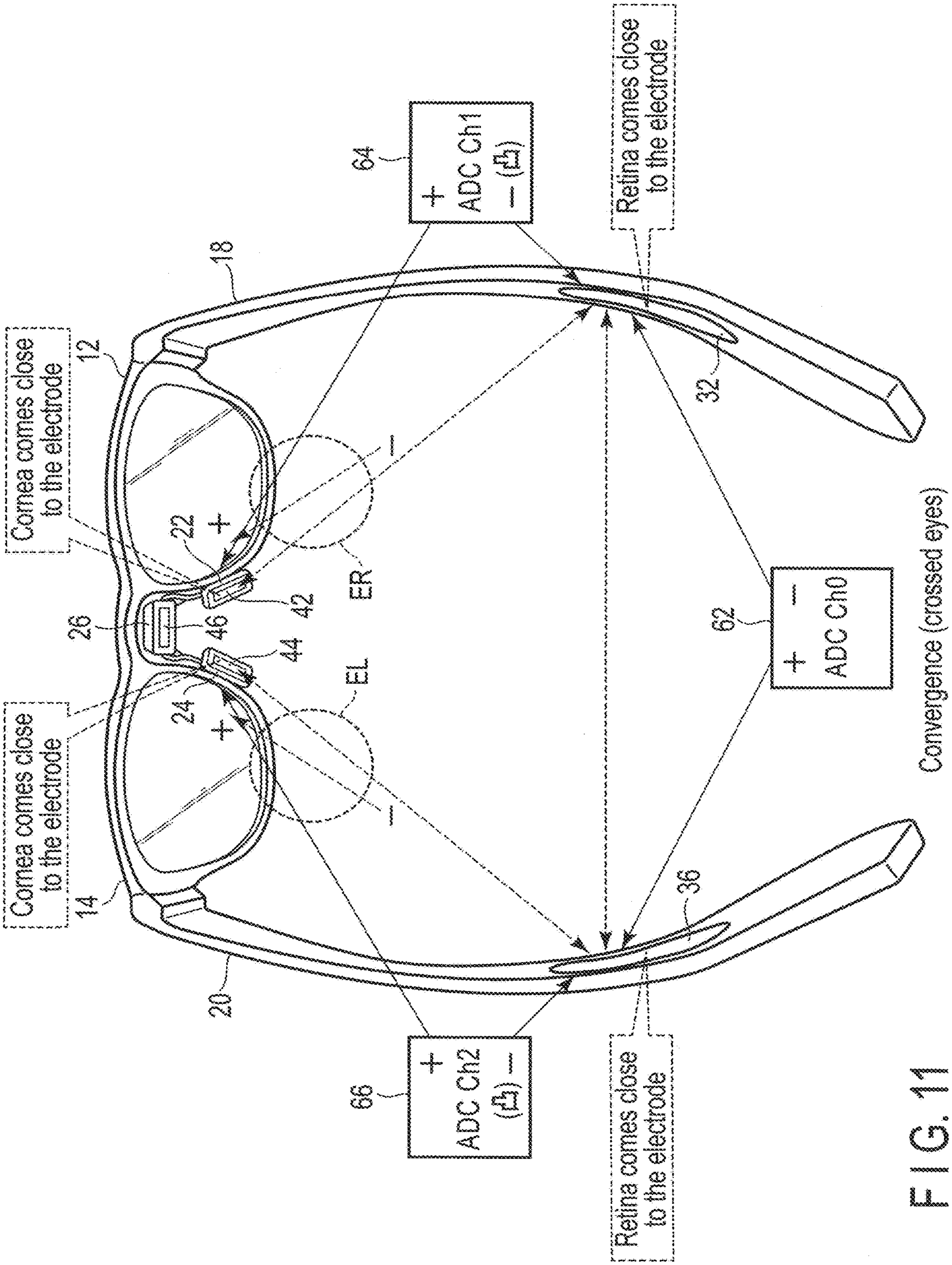
FIG. 11 shows an example of variation in a waveform of the EOG signals when the right eye and the left eye both move in a direction in which a convergence angle increases from the state where the line of sight is in the front direction.

When the right eye ER moves to the left (the line of sight of the right eye ER moves to the left) and the left eye EL moves to the right (the line of sight of the left eye EL moves to the right), as shown in FIG. 11, from the state in which the line of sight shown in FIG. 8 is in the front direction to cause convergence in which the line of sight of the right eye ER and the line of sight of the left eye EL cross, namely, when both eyes turn inward so that esotropia or "crossed eyes" occurs, the cornea of the right eye ER that is positively charged comes close to the right nose pad electrode 42, and the retina of the right eye ER that is negatively charged comes close to the right temple electrode 32. Similarly, the cornea of the left eye EL that is positively charged comes close to the left nose pad electrode 44, and the retina of the left eye EL that is negatively charged comes close to the left temple electrode 36. When the right eye ER moves to the right and the left eye EL moves to the left in this state, the state returns to that shown in FIG. 8. Thus, the first EOG signal ADC Cho output from the first analog-to-digital converter 62 to which the right temple electrode 32 and the left temple electrode 36 are connected, neither varies nor makes a convex or concave waveform. The second EOG signal ADC Ch1 output from the second analog-to-digital converter 64 to which the right nose pad electrode 42 and the right temple electrode 32 are connected, makes a convex waveform (upwardly convex waveform). The third EOG signal ADC Ch2 output from the third analog-to-digital converter 66 to which the left nose pad electrode 44 and the left temple electrode 36 are connected, makes a convex waveform (upwardly convex waveform).

Since the right eye ER and the left eye EL move in opposite directions as described above, the second EOG signal ADC Ch1 and the third EOG signal ADC Ch2 make waveforms of the same phase.

When the eye potentials of the right eye ER and the left eye EL are the same and the absolute values of rotation angles thereof are the same, a level of the positive terminal (+) and a level of the negative terminal (−) of the analog-to-digital converter 62 vary in the same direction (negative direction) by the same amount. Thus, a difference between the level of the positive terminal (+) and the level of the negative terminal (−) of the analog-to-digital converter 62 does not vary, nor does the eye potential of the first EOG signal ADC Ch0.

However, in fact, the plane including the nose pad electrode and the temple electrode is slightly shifted from the central point of the right eye ER or the left eye EL and thus a slight variation occurs in the eye potential in accordance with the amount of the shift.

Figure 12:
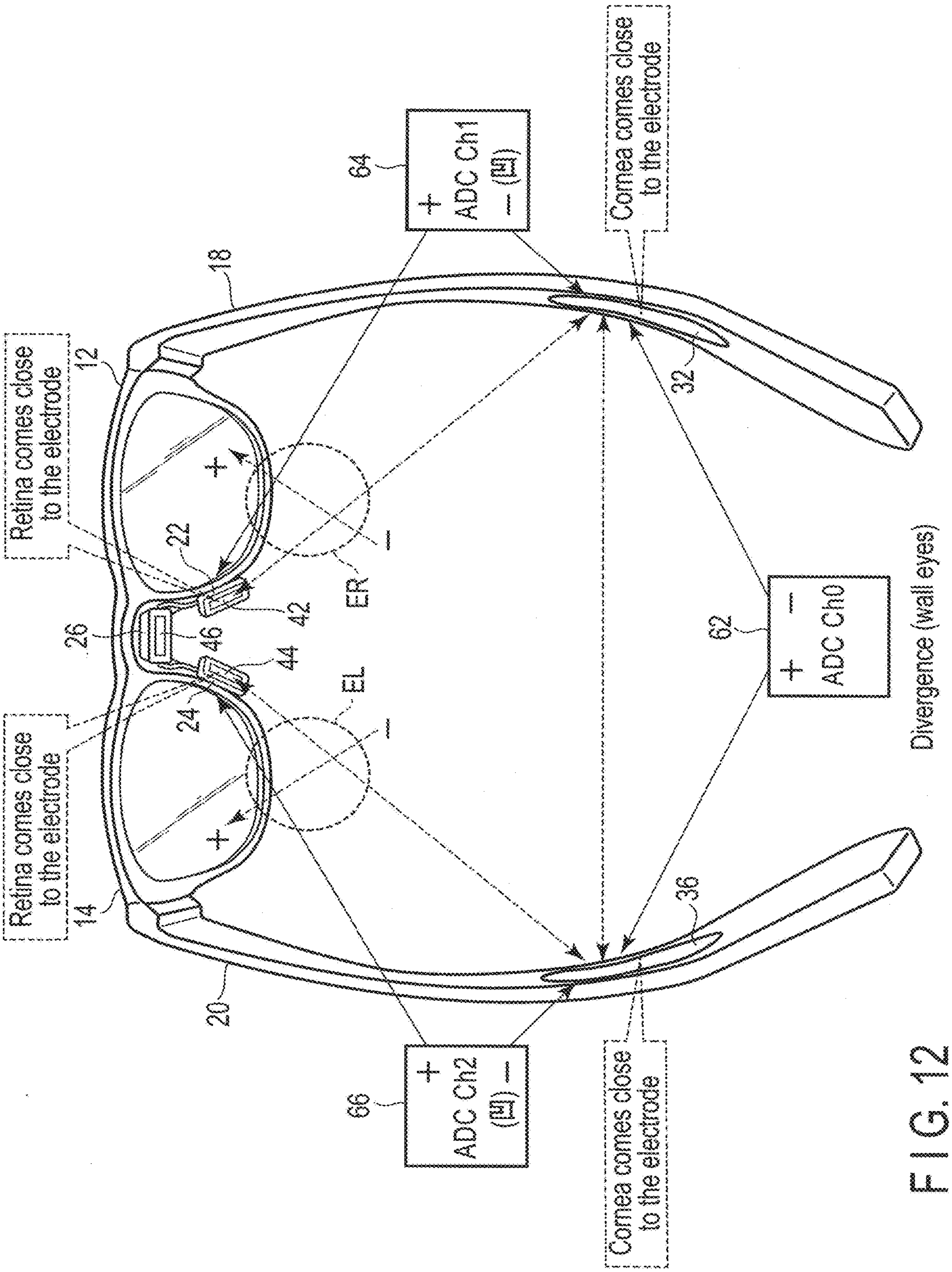
FIG. 12 shows an example of variation in a waveform of the EOG signals when the right eye and the left eye both move in a direction in which a convergence angle decreases from the state where the line of sight is in the front direction.

When the right eye ER moves to the right (the line of sight of the right eye ER moves to the right) and the left eye EL moves to the left (the line of sight of the left eye EL moves to the left), as shown in FIG. 12, from the state in which the line of sight shown in FIG. 8 is in the front direction to cause divergence in which the line of sight of the right eye ER and the line of sight of the left eye EL spread, namely, when both eyes turn outward so that exotropia or "wall eyes" occurs, the cornea of the right eye ER that is positively charged comes close to the right temple electrode 32, and the retina of the right eye ER that is negatively charged comes close to the right nose pad electrode 42. Similarly, the cornea of the left eye EL that is positively charged comes close to the left temple electrode 36, and the retina of the left eye EL that is negatively charged comes close to the left nose pad electrode 44. When the right eye ER moves to the left and the left eye EL moves to the right in this state, the state returns to that shown in FIG. 8. Thus, the first EOG signal ADC Ch0 output from the first analog-to-digital converter 62 to which the right temple electrode 32 and the left temple electrode 36 are connected, neither varies nor makes a convex or concave waveform. The second EOG signal ADC Ch1 output from the second analog-to-digital converter 64 to which the right nose pad electrode 42 and the right temple electrode 32 are connected, makes a concave waveform (downwardly convex waveform). The third EOG signal ADC Ch2 output from the third analog-to-digital converter 66 to which the left nose pad electrode 44 and the left temple electrode 36 are connected, makes a concave waveform (downwardly convex waveform). Since the right eye ER and the left eye EL move in opposite directions as described above, the second EOG signal ADC Ch1 and the third EOG signal ADC Ch2 make waveforms of the same phase. However, the phase of waveforms of the second EOG signal ADC Ch1 and the third EOG signal ADC Ch2 in "wall eyes" is opposite to that of waveforms thereof in "crossed eyes".

When the eye potentials of the right eye ER and the left eye EL are the same and the absolute values of rotation angles thereof are the same, a level of the positive terminal (+) and a level of the negative terminal (−) of the analog-to-digital converter 62 vary in the same direction (positive direction) by the same amount. Thus, a difference between the level of the positive terminal (+) and the level of the negative terminal (−) does not vary, nor does the eye potential of the first EOG signal ADC Cho. However, in fact, the plane including the nose pad electrode and the temple electrode is slightly shifted from the central point of the right eye ER or the left eye EL and thus a slight change occurs in the eye potential in accordance with the amount of the shift.

Figure 13:
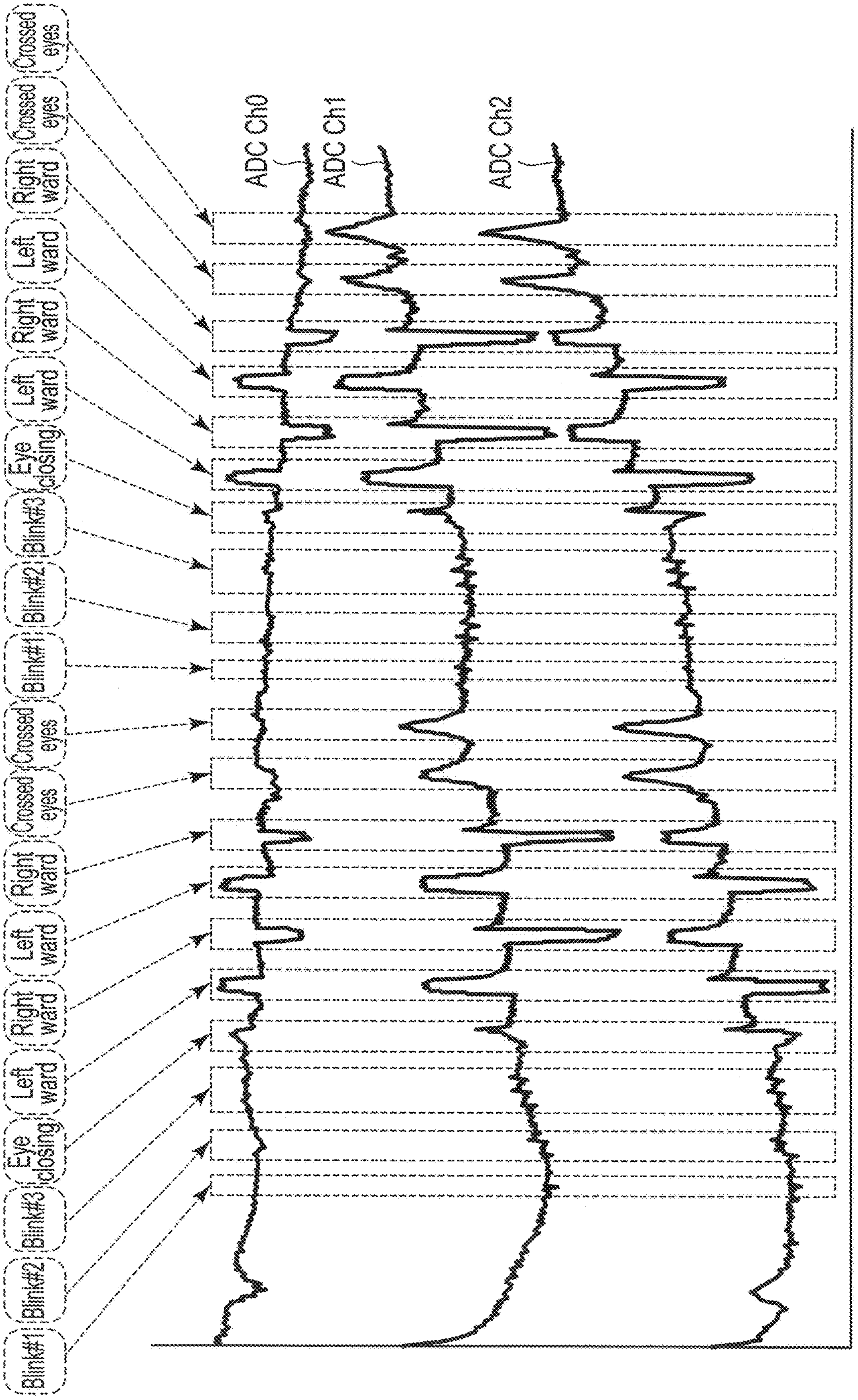
FIG. 13 is a chart showing an example of waveforms of the EOG signals for various eye movements.

FIG. 13 is a chart of eye potentials (EOG signals) illustrating an example of the relationship between various eye movements and the EOG signals ADC Ch0, ADC Ch1 and ADC Ch2 generated from the analog-to-digital converters 62, 64 and 66. In this chart, the vertical axis represents sample values of the analog-to-digital converters 62, 64 and 66 (for example, 3.3 V, 24-bit analog-to-digital converter), and the horizontal axis represents time.

As shown in FIG. 11, neither a convex waveform nor a concave waveform appears in the EOG signal ADC Ch0, but a convex waveform appears in the EOG signals ADC Ch1 and ADC Ch2, with the result that the eye movement detector 75 detects "crossed eyes" in which the line of sight of the right eye ER and the line of sight of the left eye EL are converged. As shown in FIG. 12, neither a convex waveform nor a concave waveform appears in the EOG signal ADC Cho, but a concave waveform appears in the EOG signals ADC Ch1 and ADC Ch2, with the result that the eye movement detector 75 detects "wall eyes" in which the line of sight of the right eye ER and the line of sight of the left eye EL are diverged. Since the convergence and divergence differ only in the waveform of the EOG signals ADC Ch1 and ADC Ch2 as described above, they may be collectively referred to as convergence in the following descriptions. The amplitude of the waveforms of the EOG signals ADC Ch1 and ADC Ch2 corresponds to the degree of convergence (i.e. convergence angle) and the degree of divergence. As will be described in detail later with reference to FIG. 14, the nearer the distance, the higher the degree of variation of the amplitude; and the farther the distance, the lower the degree thereof. Accordingly, the nearer the distance, the higher the sensitivity of detecting of the variation in amplitude; and the farther the distance, the lower the sensitivity thereof.

As shown in FIG. 9, a convex waveform appears in the EOG signal ADC Ch0, a convex waveform appears in the EOG signal ADC Ch1 and a concave waveform appears in the EOG signal ADC Ch2, with the result that the eye movement detector 75 detects the left movement of the line of sight.

As shown in FIG. 10, a concave waveform appears in the EOG signal ADC Ch0, a concave waveform appears in the EOG signal ADC Ch1 and a convex waveform appears in the EOG signal ADC Ch2, with the result that the eye movement detector 75 detects the right movement of the line of sight.

A first blink #1, second blink #2 and third blink #3 are respectively detected by one, two and three convex pulse waveforms of the same phase, which momentarily increase in level and returns to the original level, in the EOG signals ADC Ch1 and ADC Ch2. The eye movement detector 75 detects an eye movement in the vertical direction, namely, an eye closing by the combination of a convex waveform (upwardly convex waveform) made when the line of sight is in the upward direction and a concave waveform (downwardly convex waveform) made when the line of sight is in the downward direction in the EOG signals ADC Ch1 and ADC Ch2. The motion of the eyes caused by a blink and an eye closing in the vertical direction can be detected based at least in part on one of the EOG signals ADC Ch1 and ADC Ch2. In order to detect a blink and an eye closing only, an electrode pair need not be provided on each of the right eye ER and the left eye EL but may be provided on only one of them.

Figure 14:
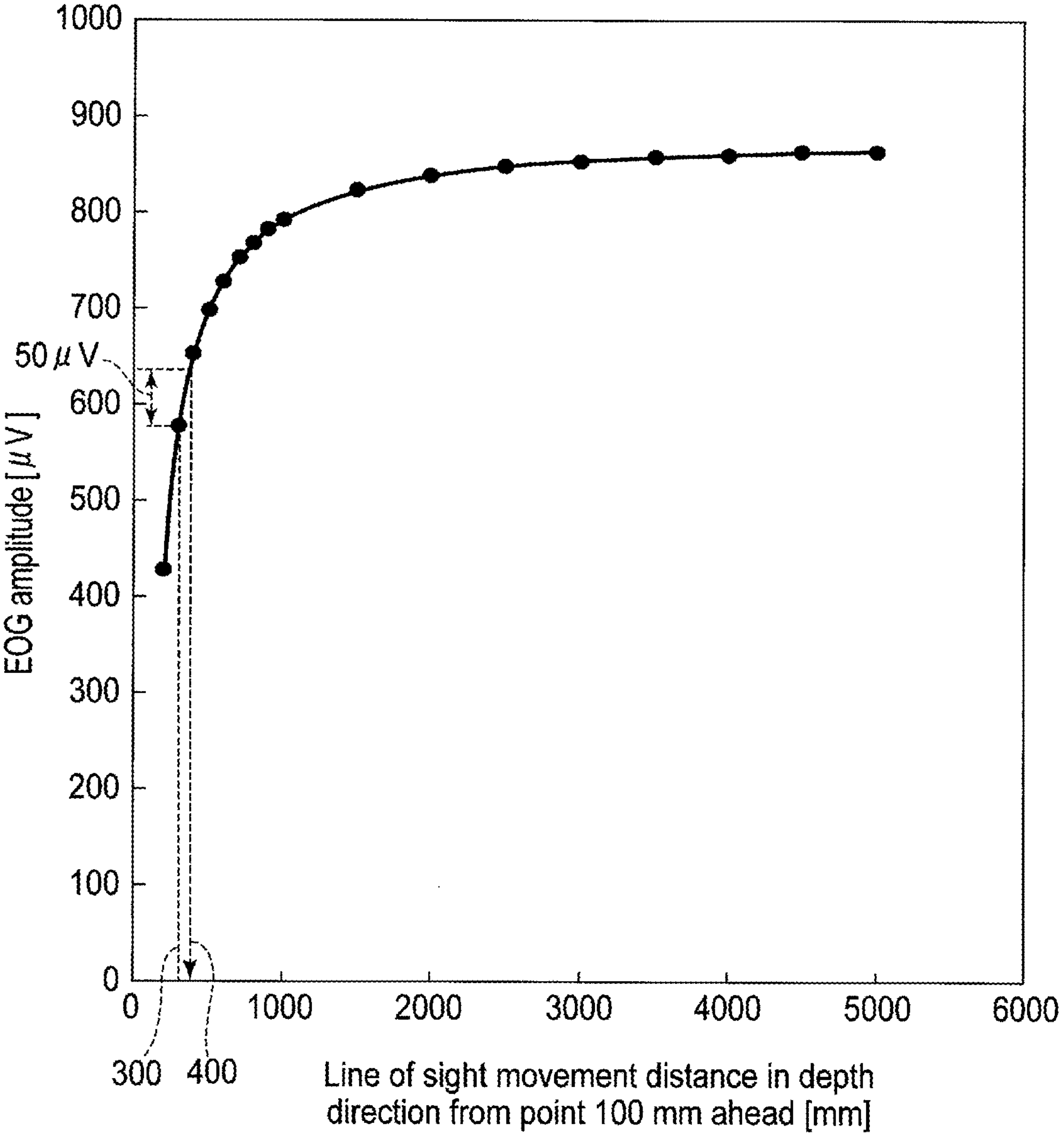
FIG. 14 is a graph showing an example of results of experiment to detect variation in convergence angle.

An example of result of experiment to detect variation in convergence angle in this embodiment will be described. FIG. 14 shows an example of variation in the second EOG signal ADC Ch1 when the intersection of the line of sight of the right eye ER and the line of sight of the left eye EL varies as a user who is looking at his or her fingertip 10 cm ahead of his or her nose looks at a farther marker, using a test model of the eye potential detector shown in FIG. 1 to FIG. 4. In this case, the intersection of the lines of sight varies from a near point to a distant point and thus the convergence angle decreases. In FIG. 14, the horizontal axis represents a distance at which the intersection of the lines of sight moves in the depth direction from a point 10 cm ahead, and the first plot represents EOG amplitude when the intersection of the lines moves from the point 10 cm ahead to a point 20 cm ahead. Note that 10 cm is the shortest distance at which the user can gaze stably. The minimum detected voltage of the EOG signal is 50 μV. In other words, if the EOG signal varies 50 μV or more, the eye movement detector 75 can detect variation in the EOG signal and based thereon, detect variation in the intersection of the line of sight, or variation in the convergence angle. If a level of the EOG signal does not vary 50 μV or more, the eye movement detector 75 cannot detect variation in the EOG signal. Note that the minimum detectable voltage of the EOG signal is 50 μV in this embodiment though it becomes lower by using an average value obtained by integrating the measured values. The amplitude of the EOG signal depends upon the contact resistance of the electrodes. If a material whose contact resistance is low is used for the electrodes, the amplitude of the EOG signal increases, as does the minimum detectable voltage of the EOG signal.

For example, when the convergence angle decreases as a user who is looking at a marker 30 cm ahead of his or her nose looks at a farther marker, if the EOG amplitude increases 50 μV, the eye movement detector 75 detects variation in EOG amplitude. The EOG amplitude obtained by adding 50 μV to the EOG amplitude caused when the user looks at a marker 30 cm ahead, corresponds to a marker 40 cm ahead. In other words, when the convergence angle decreases as a user who is looking at a marker 30 cm ahead of his or her nose looks at a marker 40 cm ahead of his or her nose looks, the eye movement detector 75 can detect variation in EOG amplitude. If variation in EOG amplitude corresponding to a decrease in convergence angle corresponding to variation of 10 cm can be detected, it can be said that the detection resolution is considerably high. It is seen from FIG. 14 that when the convergence angle decreases as a user who is looking at a marker 50 cm ahead of his or her nose looks at a marker 65 cm or more ahead of his or her nose looks, variation in EOG amplitude can be detected. When the convergence angle decreases as a user who is looking at a marker 70 cm ahead of his or her nose looks at a marker 140 cm or more ahead of his or her nose looks, variation in EOG amplitude can be detected.

As described above, according to the first embodiment, there is provided a glass-type wearable device including right and left temple electrodes, right and left nose pad electrodes and a neutral electrode placed to be influenced equally by the motion of the right eye ER and the left eye EL. A convergence angle is detected by detecting the horizontal movement of each of the right eye ER and the left eye EL independently. Since the neutral potential of the neutral electrode is considered a midpoint potential of the analog-to-digital converters that sample the EOG signals generated from the electrodes, the EOG signals are not influenced by noise. Therefore, an eye potential is accurately detected and thus an eye movement is accurately detected. According to the first embodiment, furthermore, the horizontal movement of both the right eye ER and the left eye EL (horizontal movement of the lines of sight) can be detected, as can be the vertical movement of both the right eye ER and the left eye EL.

Since the eye potential detector according to the first embodiment makes it possible to detect convergence that is a user's conscious eye movement, an application example to perform control corresponding to a user's intention can be achieved by performing control corresponding to a result of the detection. For example, in eyewear capable of AR display, the on/off operation of AR display corresponding to the detection of convergence angle and the adjustment of a display position (distance) of an AR image can be controlled in hands-free mode.

Furthermore, for an operation, variation in convergence angle peculiar to the operation may be required. If a convergence angle variation pattern is compared with a reference pattern, it is possible to check a skill level of a user of the wearable device and determine whether he or she performs the operation accurately.

An application example of convergence angle detection results will be described. The eye potential detector is incorporated into a glass-type wearable device capable of AR display to control AR display based at least in part on the convergence angle detection result. For example, the detection of convergence angle variation can be applied as a function select switch. For example, when the user sees a distant place as shown in FIG. 8, AR display is turned off. When the user changes his or her lines of sight to see a near place (convergence state) as shown in FIG. 11, the on/off state of display can be controlled to display an AR image. Since the display position of the AR image is set at a short distance, the eyes are in convergence state while the user is looking at the AR image and thus the AR display continues. If the user changes his or her lines of sight to see the distant place, the AR display is turned off. Accordingly, the AR display can be controlled as intended by the user. As a second embodiment, a surgery support glass-type wearable device of the application example will be described.

Second Embodiment

Figure 15:
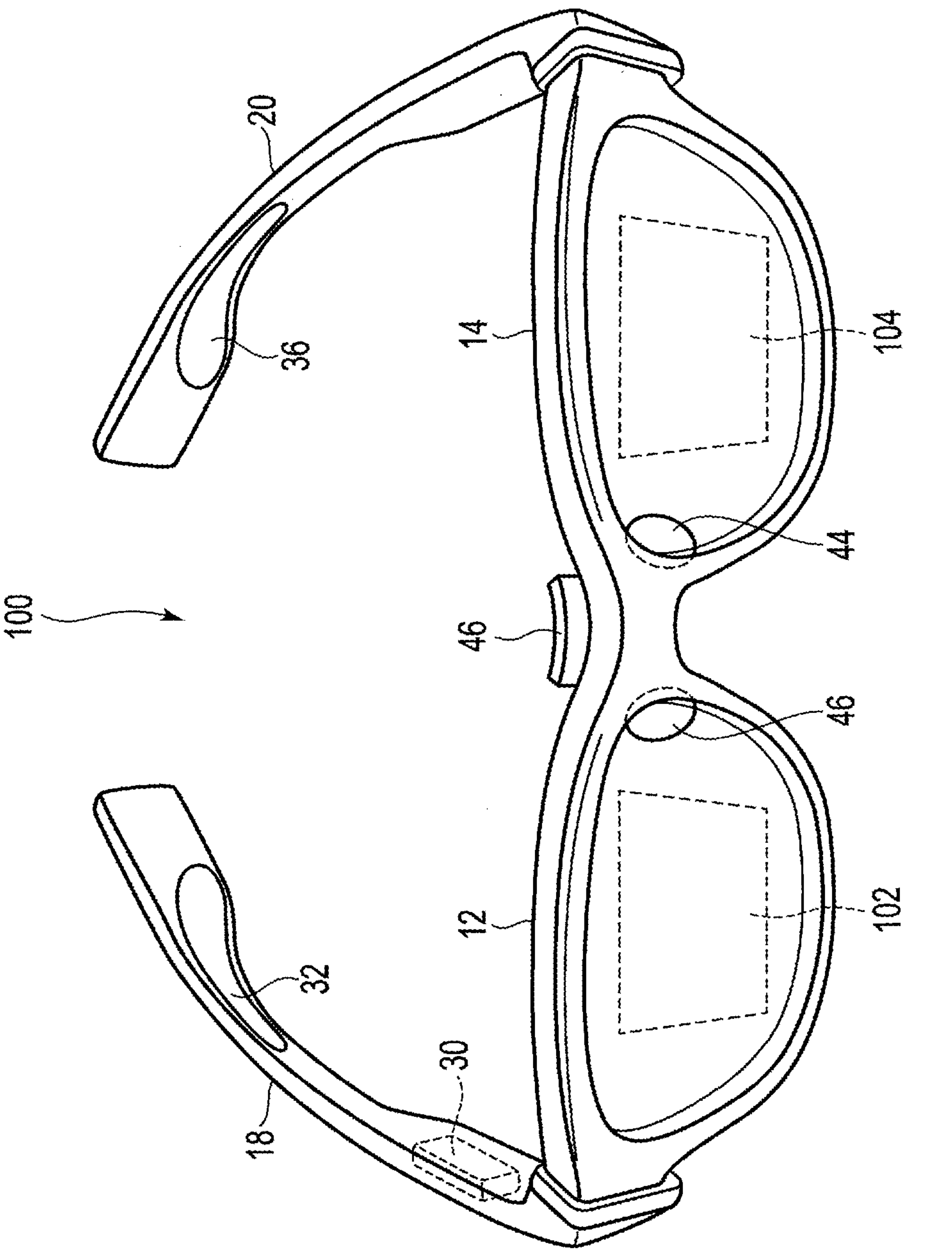
FIG. 15 is a front view of an example of a glass-type wearable device according to a second embodiment.

FIG. 15 is a front view showing an example of a glass-type wearable device 100 according to a second embodiment. The wearable device 100 of the second embodiment differs from that of the first embodiment in that displays (for example, an organic electro-luminescence panel and a liquid crystal panel) 102 and 104 for AR display are fit into at least part of the right frame 12 and the left frame 14, respectively. When augmented reality (AR) image is not displayed with in dimensions, the displays 102 and 104 need not to be fit into the right frame 12 and the left frame 14. Assume that an AR image is displayed in three dimensions. EOG electrodes are placed in the same manner as in the first embodiment. The wearable device 100, which is capable of AR display, can be applied to various examples, but an example of a surgery support system will be described as the second embodiment. Doctors who perform surgery and staff members who assist the doctors wear the wearable device 100.

Figure 16:
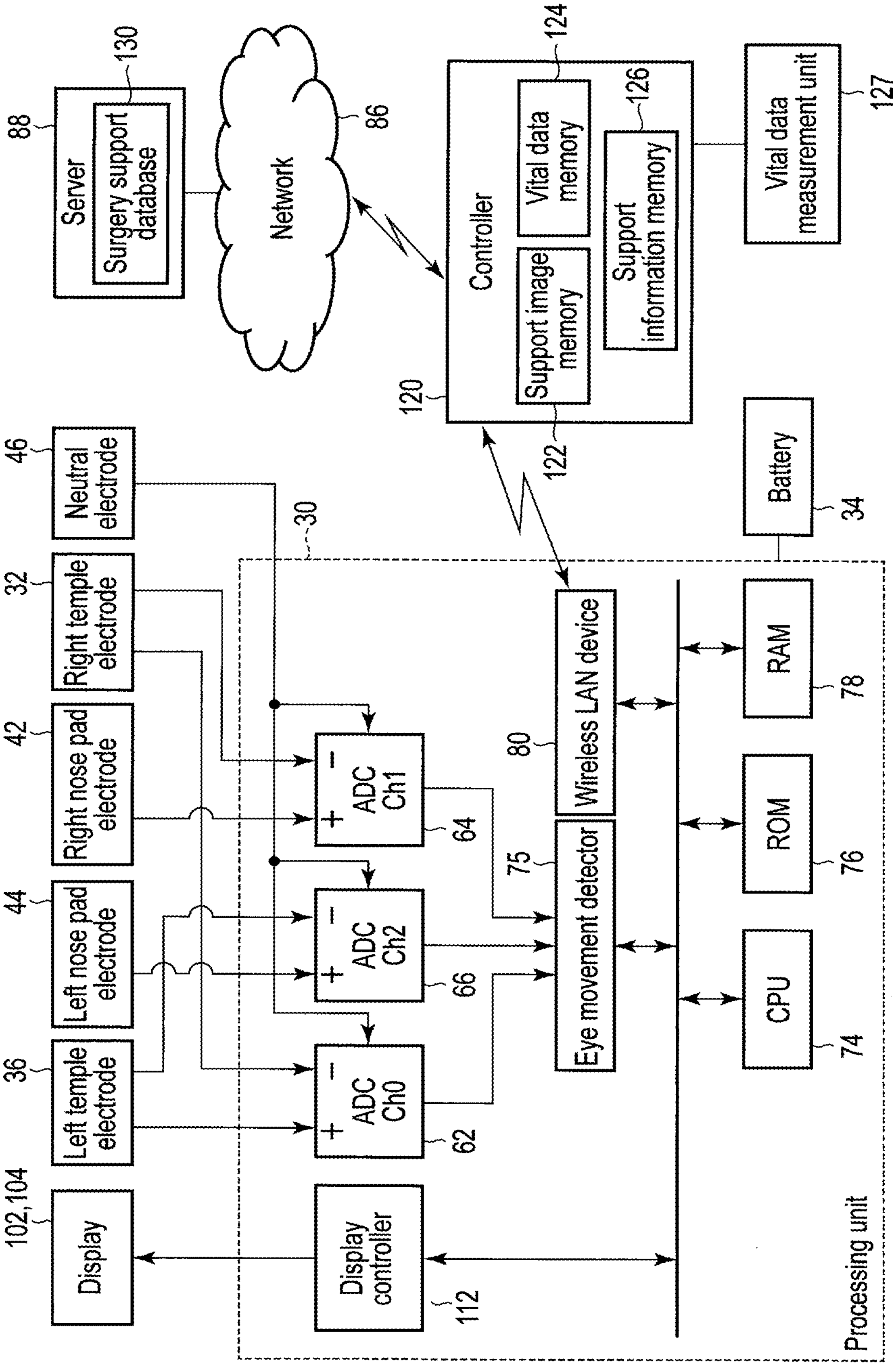
FIG. 16 is a block diagram showing an example of an electrical configuration of a surgery support system including the glass-type wearable device according to the second embodiment.

FIG. 16 is a block diagram showing an example of an electrical configuration of a surgery support system including the wearable device 100. The processing unit 30 includes a display controller 112 in addition to the configuration of the first embodiment. The display controller 112 controls AR display of the displays 102 and 104. The control of AR display includes on/off control of AR display, display position (distance) control of AR image (convergence angle control of AR image), and the like.

In the surgery support system, a plurality of doctors and staff members who are involved in the same surgery and thus a plurality of glass-type wearable devices 100 are used. Therefore, a controller 120 such as a high-performance personal computer is preferable to the mobile terminal 82 of the first embodiment such as a smartphone as a device to be connected to the processing unit 30. Though not shown, a plurality of processing units 30 are connected to the controller 120. The controller 120 includes a vital data memory 124, a support image memory 122 and a support information memory 126. The eye movement detector 75 may not be provided in the processing unit 30. The controller 120 may include an eye movement detector 75.

A vital data measurement unit 127 is connected to the controller 120 to measure an electrocardiogram, a blood pressure, a pulse and the total amount of transfused blood for each patient. These vital data items are stored in the vital data memory 124 in the controller 120 for each patient. The support image memory 122 stores support images to support surgery. When necessary, the support images in a surgery support database 130 in the server 88 are downloaded to the controller 120 and stored in the support image memory 122. The support information memory 126 stores a support text for surgery support. When necessary, the support texts in the surgery support database 130 in the server 88 are downloaded to the controller 120 and stored in the support information memory 126.

Figure 17A:
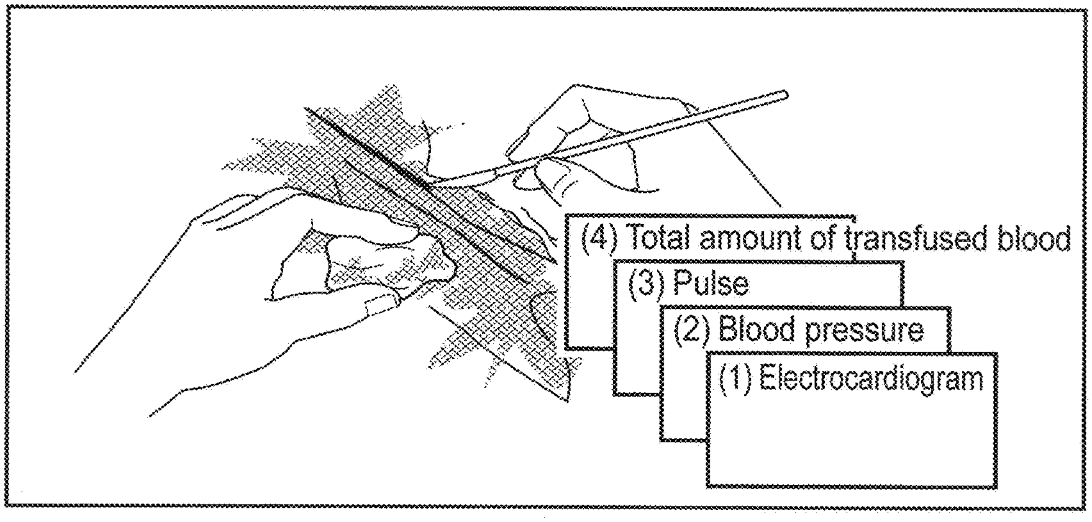
FIG. 17A, FIG. 17B and FIG. 17C show an example of an operation of the glass-type wearable device according to the second embodiment.

An example of an operation of the wearable device 100 will be described with reference to FIG. 17A to FIG. 17C, FIG. 18A and FIG. 18B. Assume that the distance from the user's eyes to an affected area under surgery (real world) is about 40 cm. When the user looks at a point between the user and the affected area (real world), for example, a point about 30 cm distant from the user's eyes, the eye movement detector 75 detects variation in the convergence angle of the user. As shown in FIG. 11, the eye movement detector 75 detects convergence based at least in part on a fact that the waveform of EOG signal ADC Ch0 does not vary and that the waveforms of EOG signals ADC Ch1 and ADC Ch2 become upwardly convex. When the eye movement detector 75 detects convergence, it requests an AR image regarding support for the surgery for the controller 120 and causes the display controller 112 to display the AR image. As an example of the AR image, a vital data window (AR image) is translucently overlapped with the affected area under surgery (real world) as shown in FIG. 17A. The window includes a plurality of pages, and each of the pages displays an electrocardiogram, a blood pressure, a pulse, the total amount of transfused blood and the like. The window is limited to a region of the display to prevent the affected area from being hidden. In response to the request from the processing unit 30, the controller 120 reads the vital data of the patient from the vital data memory 124 and transfers it to the processing unit 30.

If a distance between the right image and the left image of the AR image is adjusted when the AR image is displayed in three dimensions, the display position (distance) of the AR image can optionally be set. Here, the display position of the vital data window is set in a position about 30 cm ahead of the user's eyes, the about 30 cm being equal to a distance at which the eye movement detector 75 detects convergence of the lines of sight of the user. When the vital data window is displayed, the user looks at the position about 30 cm ahead of the user's eyes. Therefore, the user can confirm the contents of the vital data window instantly and need not move his or her eyes or adjust the convergence angle of the lines of sight to gaze at the window, which causes no eyestrain.

Figure 17B:
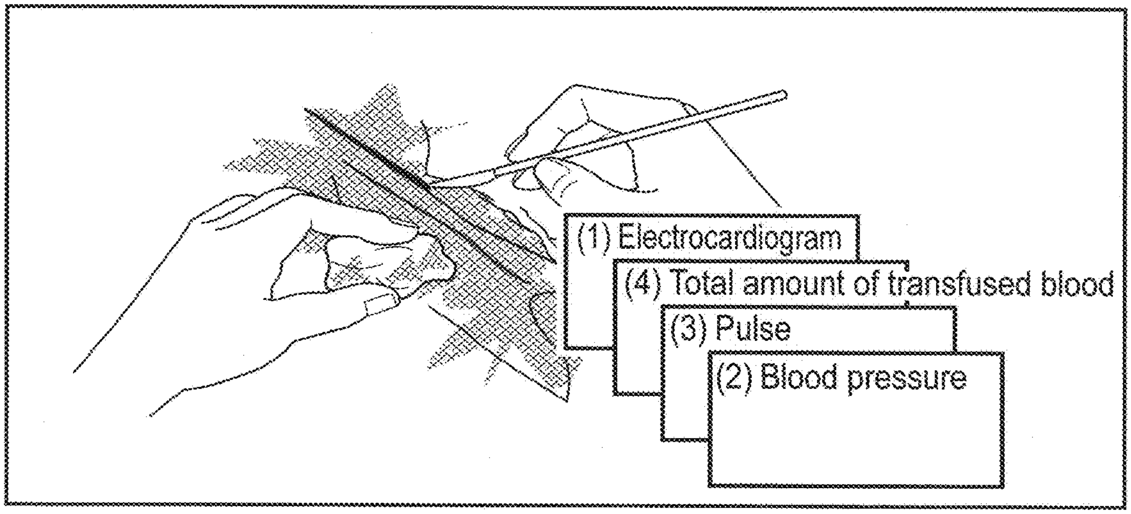

The pages of the vital data window can be switched automatically every fixed time period, for example, every one second or switched with user's intention based at least in part on the eye movement in another direction detected by the eye movement detector 75. If an eye closing of for example, 0.5 seconds or longer is detected, a page of the vital data window can be switched. For example, a page can be switched to the following page when the line of sight moves to the right and switched to the preceding page when the line of sight moves to the left. FIG. 17B shows an example in which a page of the window is switched.

In the state shown in FIG. 17A and FIG. 17B, when, for example, the user changes his line of sight to look at the affected area (real world) under surgery (a point about 40 cm more distant), the eye movement detector 75 detects that the convergence angle decreases (the distance to the intersection of the lines of sight of both the eyes increases) and causes the display controller 112 to stop the AR display. Therefore, for example, the user observes only the affected area under surgery as shown in FIG. 17C through the right frame 12 and the left frame 14 of the glasses.

Figure 17C:
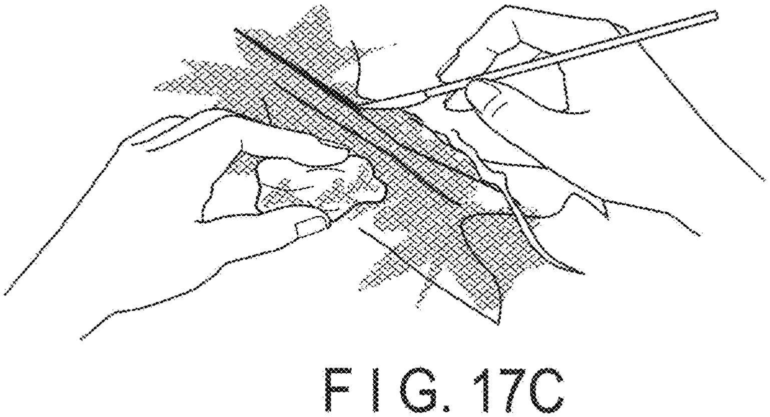

When, for example, the user wishes to refer to vital data in the state shown in FIG. 17C, he or she changes his or her lines of sight to look at his or her nearby point (about 30 cm distant from the user). The eye movement detector 75 detects that the convergence angle increases (the distance to the intersection of the lines of sight of both the eyes decreases) and causes the display controller 112 to make AR display, with the result that a vital data window as shown in FIG. 17A or FIG. 17B is displayed.

The determination that the convergence angle increases or decreases is based at least in part on the relationship between the EOG amplitude and the movement distance of the intersection of the lines of sight as shown in FIG. 14. It can be determined that the convergence angle has increased or decreased when an EOG voltage decreases or increases by a certain value.

As described above, the user can turn on or off AR display for surgery support in hands-free mode during the surgery. This brings about a significant advantage because the user's hands are busy during the surgery.

Figure 18A:
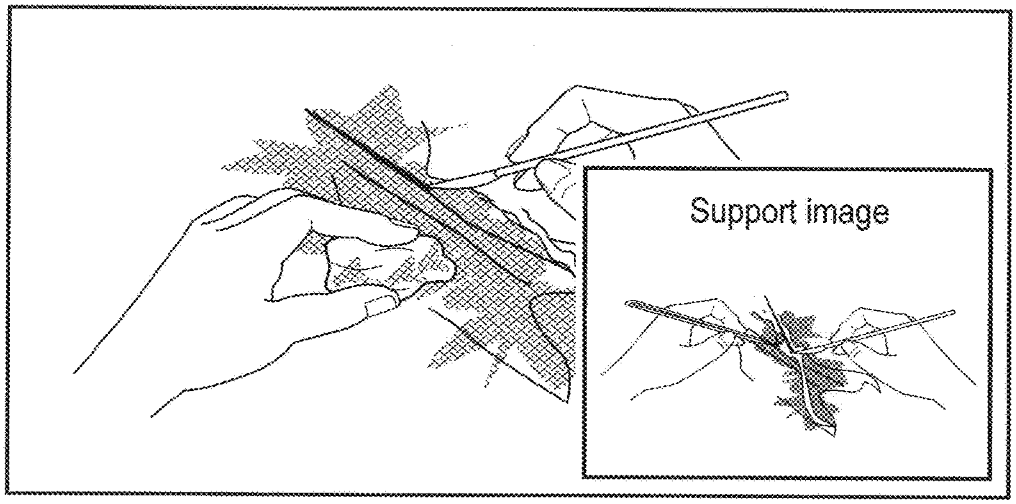
FIG. 18A and FIG. 18B show another example of the operation of the glass-type wearable device according to the second embodiment.
Figure 18B:
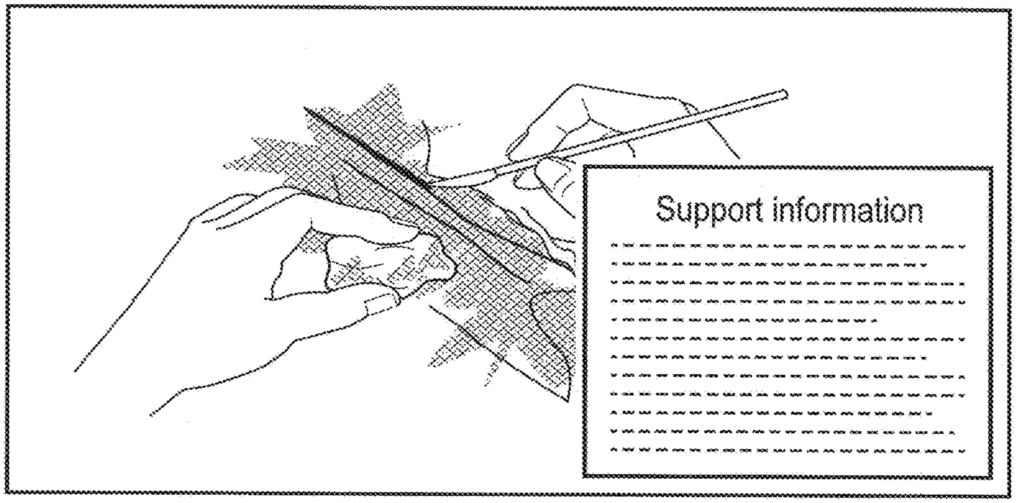

As another example of the AR display, a support image can be displayed as shown in FIG. 18A. The support image may include an image of an example of the past surgery for a patient who is in similar condition and an image of other surgery for the patient. The image may include a still image and a moving image. An image of surgery is captured by a camera (not shown), and the captured image is uploaded to the server 88 and stored in the surgery support database 130. As still another example of the AR display, support information can be displayed as shown in FIG. 18B. The support information includes various items of text data regarding surgery that is being performed.

The display position (distance) of the support information is set close to the user, like that of the vital data window. However, the display position of the support image can be set at a distance of about 40 cm from the user, like that of the affected area under surgery (real world). The user does not see the vital data window or the support information simultaneously with the affected area under surgery. But it is assumed that the user sees the support image simultaneously with the affected area under surgery to compare them. If the affected area and the support image differ in display position when they are compared, the user needs to adjust focus by moving his or her eyes in the horizontal direction and thus could get eyestrain. For this reason, unlike in the foregoing description, the support image may be displayed when the eyes are in a state as shown in FIG. 8 and turned off when convergence is detected as shown in FIG. 11. If the display position of the support image is subtly shifted from the affected area under surgery (real world) when they are compared, a convergence angle detected by the eye movement detector 75 is subtly changed. If the display controller 112 adjusts the display position (convergence angle between the right and left images) of the support image to decrease the convergence angle variation detected by the eye movement detector 75, the possibility of causing eyestrain can be lowered further.

The switching from the vital data window to the support image and support information can be performed by the user based at least in part on an eye movement in another direction detected by the eye movement detector 75, like the switching of pages of the vital data window.

In the foregoing example, the on/off switching of AR display is performed by the convergence angle variation of the user; however, the detected convergence angle can be used for other control and the on/off switching can be based at least in part on another eye movement. For example, when eye closing is detected more than once, the AR display can be switched between on and off states. The detected convergence angle can be used to control the display position of the AR image. In other words, the distance between the right image and the left image of the AR image (which is also referred to as a convergence angle of the AR image) is adjusted based at least in part on the distance to the intersection of the line of sight of the right eye ER and the line of sight of the left eye EL at the start of the display of the AR image. The convergence angle of the AR image is adjusted by the display controller 112. Thus, the user need not move his or her eyes in the horizontal direction to gaze at the AR display, which causes no eyestrain.

Another application example of the convergence angle variation and the control of AR display will be described with reference to FIG. 19A and FIG. 19B. This example is directed to a pickup operation in a warehouse. During the pickup operation, a user wears the wearable device 100.

The configuration of the processing unit 30 is not shown because it is the same as that shown in FIG. 16. The configuration of the controller 120 is not shown because it differs only in that a pickup list is used in place of the vital data, support image and support information. As in the first embodiment shown in FIG. 4, the mobile terminal 84 such as a smartphone can be used in place of the controller 120. The mobile terminal 84 may acquire position information. The configuration of the server 88 is not shown because it differs only in that map information about the positions of shelves in the warehouse, a list of goods on the shelves, and a list of goods to be picked up are used in place of the surgery support data. The pickup list for each user is downloaded to the controller 120 from the server 88.

In this application example, too, AR display is first turned off, and the displays 102 and 104 of the right and left frames 12 and 14 display nothing and are therefore transparent. The user thus gazes at the inside of the warehouse, as shown in FIG. 19A and FIG. 19B, through the right frame 12 and the left frame 14. When the mobile terminal 84 as the controller 120 can acquire position information, air tags can be displayed on goods on each shelf based at least in part on the map information in the server 88 and the acquired position information. The user then sees several meters or several tens of meters ahead.

When the user moves his or her right eye ER and left eye EL horizontally in opposite directions to cause convergence or "crossed eye" as the user who is looking at a distance point looks at a near point, the eye movement detector 75 detects the convergence. In accordance with the detection of the convergence, the processing unit 30 requests for the controller 120 a pickup list indicating goods to be picked up by the user and causes the display controller 112 to start AR display. An example of the pickup list is shown in FIG. 19A and FIG. 19B. The display position of the pickup list is set close to the user. When the user moves his or her right eye ER and left eye EL to change from a state in which he or she looks at the pickup list to a state in which he or she looks at the warehouse that is distant, as shown in FIG. 8, the eye movement detector 75 does not detect the convergence. Thus, it causes the display controller 112 to stop the display of the pickup list.

Like during the surgery, during the pickup operation, the user's hands are busy. Thus, a significant advantage in which the AR display can be switched between on and off states in hands-free mode is brought about.

Figure 19A:
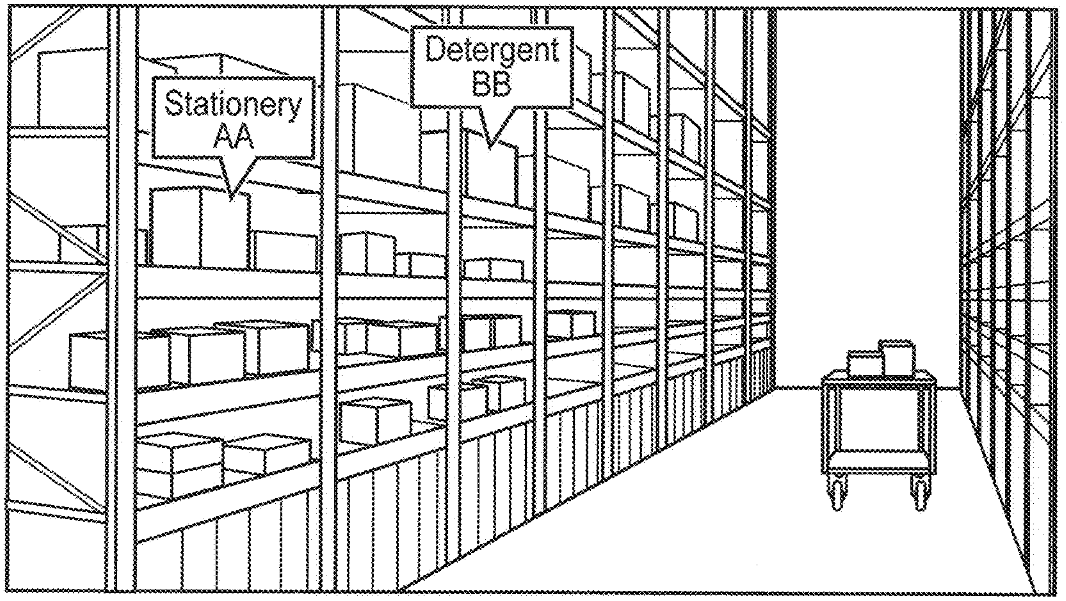
FIG. 19A and FIG. 19B show a still another example of the operation of the glass-type wearable device according to the second embodiment.
Figure 19B:
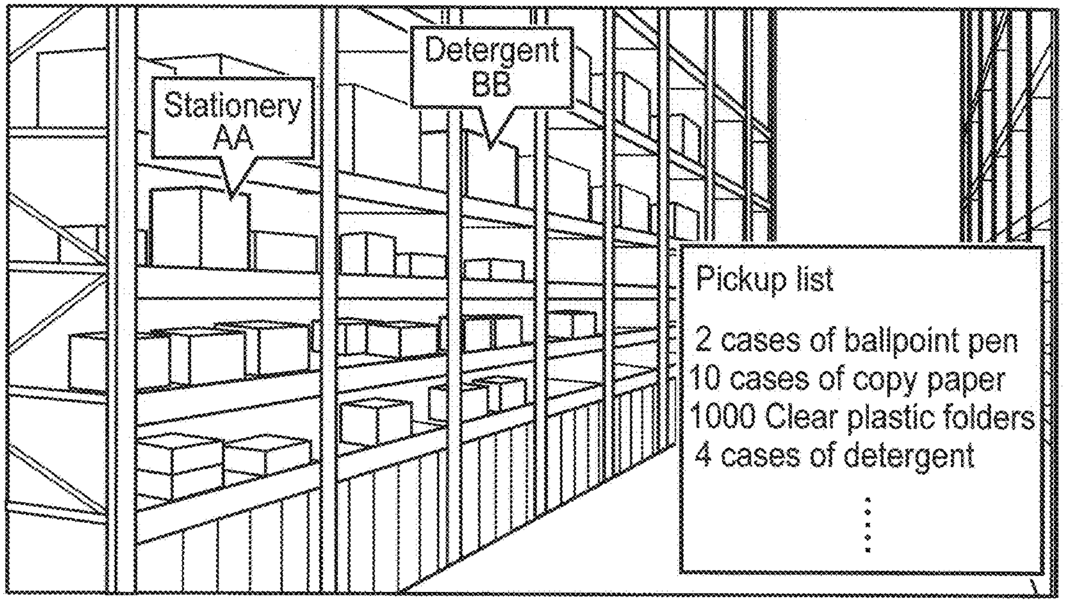

In FIG. 19A and FIG. 19B, the air tag is displayed at all times; however, it can be displayed only when a user looks at a distant target object and turned off when the user looks at a nearby target object in another example. Assume that a user goes out to perform elevator maintenance in a building. While the user is looking for the target building on his or her way, he or she is looking at a distant target object; thus, an air tag indicative of the name of the building, the distance, the purpose of the maintenance, etc., is displayed on the target building. When the user looks at his or her nearby point to read a map or the like, the air tag may be turned off. When the user arrives in front of the elevator in the target building and looks at a portion to be inspected, an air tag is displayed on the portion. When the user looks at his or her nearby point, an AR image of an operation manual, etc., is displayed in place of the air tag. This example can be applied to a tourist guide. For example, while a tourist is seeing a scene in a tourist spot, an air tag concerning the spot can be displayed and when he or she looks at his or her nearby point, the air tag can be turned off and a detailed tourist guide can be displayed instead.

As another example of making AR display by sensing convergence, it is considered that the eye potential detector is incorporated into AR glasses for sports watching. Images of situations of a game are picked up at various angles and stored in a server as replay images. The AR glasses are connected to the server via a network. Spectators always watch the game and see the distant target object. At that time, the AR display is turned off. When the spectators in bleacher seats of a baseball stadium wish to see an enlarged image of close play on the home plate, they move their eyes to become cross-eye to start AR display. In the AR display, various replay images are downloaded from the server and displayed. The spectators can thus enjoy the replay images instantaneously by their eyes' motion.

In the foregoing descriptions, AR display is started when convergence is detected, and it is stopped when no convergence is detected. The opposite is true and in other words, AR display can be made when no convergence is detected, and it can be stopped when convergence is detected.

Third Embodiment

Figure 20:
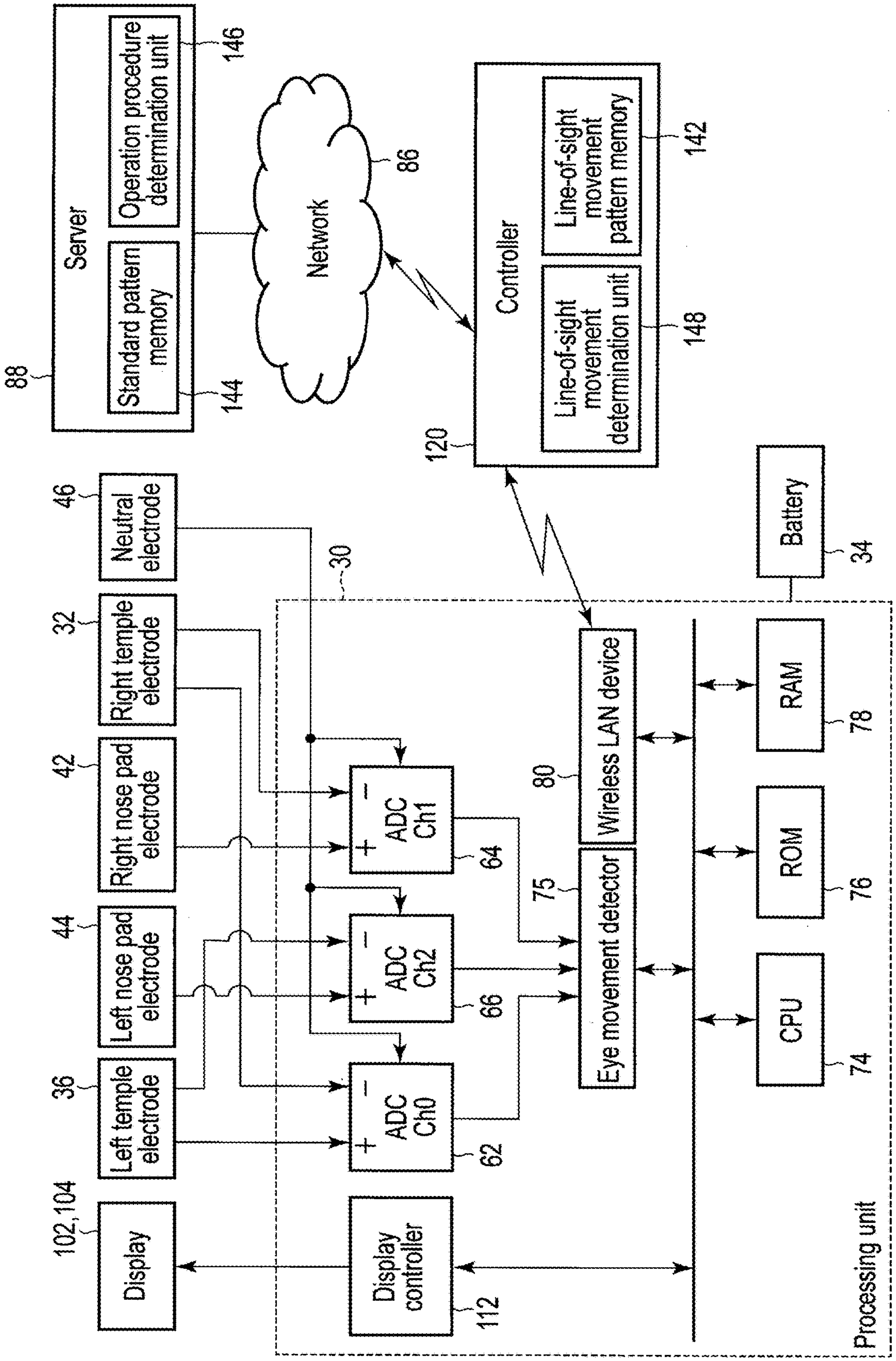
FIG. 20 is a block diagram showing an example of an electrical configuration of a system including a glass-type wearable device according to a third embodiment.

As another application example of the convergence detection, there is confirmation of an operation procedure. FIG. 20 is a block diagram showing an example of an electrical configuration of an operation confirmation system including a glass-type wearable device. Though AR display is not essential to the operation confirmation, it can be used to transmit a confirmation result to a user immediately. The processing unit 30 of the third embodiment is the same as that of the second embodiment shown in FIG. 16. Instead of the controller 120, a mobile terminal 84 such as a smartphone can be used as in the first embodiment shown in FIG. 4. The controller 120 includes a line-of-sight movement determination unit 148 and a line-of-sight movement pattern memory 142. The line-of-sight movement determination unit 148 determines the direction of line-of-sight movement (rightward movement, leftward movement, intersection of the lines of sight (convergence)) from variation pattern of eye movement detected by the eye movement detector 75, and stores a line-of-sight movement pattern in the line-of-sight movement pattern memory 142. Data of the line-of-sight movement pattern memory 142 is uploaded to the server 88 via the network 86.

The server 88 includes a line-of-sight movement standard pattern memory 144 and an operation procedure determination unit 146. The operation includes an operation in which line-of-sight movement peculiar to the operation is required. For example, in the railroad industry, the station staff is required to confirm a distant target object and a nearby target object in prescribed order by pointing his or her finger after a train has departed. In visual inspection of structures such as a bridge and a tunnel, too, an inspector is required to move his or her lines of sight in a prescribed pattern because portions to be viewed are predetermined. The standard pattern memory 144 stores a standard pattern of movement of lines of sight peculiar to such an operation. The operation procedure determination unit 146 compares the user's lines-of-sight movement pattern uploaded from the controller 120 with the standard pattern in the standard pattern memory 144 to determine whether the user performs his or her operation accurately. The standard pattern may be stored in a database (not shown) for each user. In accordance with the variation in results of the determination as time passes, improvement of the user's skill can be estimated. Alternatively, when the operation procedure determination unit 146 determines that the user does not perform the operation accurately, it may notify the display controller 112 of the processing unit 30 of that effect via the controller 120 and display a warning message on the displays 102 and 104.

As another example of the line-of-sight movement standard pattern, there is a car driving pattern. In driver education for driver license renewal, a superior driver's confirmation of safety conditions may be introduced on video. The drivers in the driver education may not only watch the video but also follow the superior driver's confirmation. The line-of-sight movement pattern is detected when the drivers follow the superior driver's confirmation. The detected line-of-sight movement pattern of the driver is compared with that of the superior driver to determine the drivers' skill in confirming safety conditions. In the transportation industry, too, if a beginner driver learns the same line-of-sight movement pattern as that of an expert driver, car accidents can be reduced.

The foregoing descriptions are not limited to glasses but can be applied to goggles. For example, an electrode can be provided on the front of the goggles in place of the node pads, and an electrode can also be provided on the belt of the goggles in place of the temples.

Calibration

In the electrooculography, no specific angle is obtained as the convergence angle, but only the motion direction of the eyes that is brought into a convergence state is obtained. In the foregoing embodiments, therefore, convergence is detected and in the application examples, control is performed based at least in part on two states in which convergence is detected or not, irrespective of the convergence angle. However, when there are plural target objects at different known distances, the target objects are seen and an eye potential is regularly measured for the different known distances. As a result, an eye potential for the different known distances can be obtained and three or more convergence states can be recognized. For example, AR display is turned off when a user looks at a distant target object, a first AR image is displayed when the user looks at a middle-distance target object, and a second AR image is displayed when the user looks at a nearby target object.

Note that since the contact resistance of the electrodes varies (lowers with time), the absolute value of the eye potential relative to the distance varies with time and the absolute value of the distance cannot be assured for a long time. For example, the contact resistance is high immediately after the start of use of the electrodes. Thus, the amplitude of the EOG signal is small and the resistance lowers with time, and the amplitude of the EOG signal increases. If, however, the eye potential relative to the distance is regularly calibrated, the variation of the eye potential with time can be estimated and the absolute value of the eye potential relative to the distance can be assured. For example, in an operation with a fixed focal length, such as surgery and desk work and a business operation that assures that a target object with a known distance is seen at a point in time in the operation process, the eye potential can regularly be calibrated in the known state of the distance.

Though the potential of the human body may vary, this variation can be compensated by regular calibration.

Summary of Embodiments

According to the foregoing embodiments, since the horizontal movement of the right eye ER and that of the left eye EL can be detected independently, convergence that is an intersection of the line of sight of the right eye ER and the line of sight of the left eye EL can be detected. The convergence is caused not unconsciously but by user's conscious eye movement. Hands-free control can thus be performed according to a user's intention by performing control in accordance with the detection of the convergence. For example, in a glass-type wearable device that makes AR display, the AR display can be started when the user becomes "crossed eye" state and it can be finished when the user looks at a distant target object.

The AR display includes monocular display and binocular display. The foregoing embodiments can also be applied to the monocular display; however, the binocular display brings about the advantage of detecting convergence of the AR image (an interval between the right eye ER and the left eye EL). In displaying an AR image in three dimensions for binocular display, an interval between the right image and the left image (which is also referred to as a convergence angle) is optionally set. If the convergence angle of the lines of sight of the right eye ER and the left eye EL of a user who is seeing the real world and the convergence angle of the AR image differ from each other, the convergence angle of the lines of sight of the right eye ER and the left eye EL has to be adjusted when the real world and the AR image are compared, which causes eyestrain. If, however, the convergence angle of the AR image is set to coincide with that of the lines of sight of the right eye ER and the left eye EL, the user need not move his or her right eye ER and left eye EL to adjust the convergence angle, which causes no eyestrain.

Variation in motion of a user's eyes is detected during his or her operation, and an elapsed-time pattern of the variation is obtained and compared with the standard pattern. Accordingly, the contents of the operation can objectively be confirmed. For example, in an operation such as maintenance and inspection, when it is necessary to confirm a distant target object and a nearby target object, it is possible to confirm whether the operation is performed according to the procedures by detecting convergence during the operation. A result of the confirmation can be notified to the user as an alarm. The embodiments can also be applied to finger-pointing confirmation after a train has departed, as well as the maintenance and inspection.

The comparison with the standard pattern can be used for skill in operation procedures with convergence as well the confirmation of the contents of the operation. For example, in driver education for driver license renewal, a superior driver's confirmation of safety conditions may be introduced on video. The drivers in the driver education not only watch the video but also follow the superior driver's confirmation. The line-of-sight movement pattern is detected when the drivers follow the superior driver's confirmation. The detected line-of-sight movement pattern of the driver is compared with that of the superior driver to determine the drivers' skill in confirming safety conditions. Thus, the drivers in the driver education understand an ideal convergence variation in detail.

Note that the horizontal movement of eyes is not limited to the motions (convergence) of the right eye ER and the left eye EL in opposite directions but includes the rightward movement of the line of sight and the leftward movement of the line of sight in which the right eye ER and the left eye EL move in the same direction. These movements can be combined with the detection of convergence to perform hands-free control. Nystagmus can be detected based at least in part on the rightward movement of the line of sight and the leftward movement of the line of sight, which are caused together with the convergence when a user feels sleepy. The alarm can thus be given to the user who feels sleepy. Hands-free control can be performed by detecting the eye movement in the vertical direction as well as in the horizontal direction and combining the eye horizontal and vertical movements.

The present invention is not limited to the foregoing embodiments themselves. When the invention is reduced to practice, its structural elements can be modified and embodied without departing from the spirit of the invention. Furthermore, a variety of inventions can be made by appropriate combinations of the structural elements of the embodiments. For example, some of the structural elements of the embodiments can be omitted. Moreover, the structural elements of different embodiments can be combined appropriately.

What is claimed is:

1. A wearable device comprising:

a frame worn by a user and comprising a display configured to display a real world and an augmented reality image;

a detector configured to detect a right eye movement of a right eye of the user, a left eye movement of a left eye of the user, and a convergence angle at which a line of sight of the right eye and a line of sight of the left eye of the user intersect based on the right eye movement and the left eye movement, wherein a first convergence angle is detected when the user looks at a first object at a first distance in the real world, a second convergence angle is detected when the user looks at a second object at a second distance in the real world, and the first distance is shorter than the second distance; and a processor configured to cause the display to display an augmented reality image when the detector detects the second distance, the augmented reality image comprising a name of the second object, and to stop display of the augmented reality image when the detector detects the first distance.

2. The wearable device of claim 1, wherein the processor is configured to transmit a request signal to an electronic device and receive the augmented reality image transmitted from the electronic device in response to the request.

3. A display method for a wearable device comprising a frame worn by a user and comprising a display configured to display a real world and an augmented reality image; and a detector configured to detect a right eye movement of a right eye of the user, a left eye movement of a left eye of the user, and a convergence angle at which a line of sight of the right eye and a line of sight of the left eye of the user intersect based on the right eye movement and the left eve movement wherein a first convergence angle is detected when the user looks at a first object at a first distance in the real world, a second convergence angle is detected when the user looks at a second object at a second distance in the real world, and the first distance is shorter than the second distance the method comprising:

causing the display to display an augmented reality image when the detector detects the second distance, the augmented reality image comprising a name of the second object; and causing the display to stop display of the augmented reality image when the detector detects the first distance.

4. The method of claim 3, further comprising:

transmitting a request signal to an electronic device; and receiving the augmented reality image transmitted from the electronic device in response to the request.

* * * * *